(12) United States Patent
Melnyk et al.

(10) Patent No.: US 9,206,224 B2
(45) Date of Patent: Dec. 8, 2015

(54) METHOD FOR SYNTHESIZING PROTEINS

(71) Applicant: CENTRE NATIONAL DE LA RECHERCHE SCIENTIFIQUE (CNRS), Paris (FR)

(72) Inventors: Oleg Melnyk, Annoeullin (FR); Laurent Raibaut, Nice (FR); Vincent Aucagne, Fleury-Les-Aubrais (FR); Agnes Delmas, Orleans (FR)

(73) Assignee: CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 0 days.

(21) Appl. No.: 14/352,155

(22) PCT Filed: Oct. 16, 2012

(86) PCT No.: PCT/EP2012/070454
§ 371 (c)(1),
(2) Date: Apr. 16, 2014

(87) PCT Pub. No.: WO2013/057084
PCT Pub. Date: Apr. 25, 2013

(65) Prior Publication Data
US 2014/0256879 A1    Sep. 11, 2014

(30) Foreign Application Priority Data

Oct. 17, 2011 (FR) ..................................... 11 59348

(51) Int. Cl.
| | | |
|---|---|---|
| A61K 38/00 | (2006.01) | |
| C07K 5/00 | (2006.01) | |
| C07K 7/00 | (2006.01) | |
| C07K 1/107 | (2006.01) | |
| C07K 1/02 | (2006.01) | |
| C07K 1/04 | (2006.01) | |
| C08F 8/34 | (2006.01) | |

(52) U.S. Cl.
CPC ............... *C07K 1/1077* (2013.01); *C07K 1/026* (2013.01); *C07K 1/04* (2013.01); *C07K 1/042* (2013.01); *C07K 1/045* (2013.01); *C08F 8/34* (2013.01)

(58) Field of Classification Search
None
See application file for complete search history.

(56) References Cited

U.S. PATENT DOCUMENTS

| 7,884,182 B2 | 2/2011 | Botti et al. | |
|---|---|---|---|
| 2002/0132975 A1 * | 9/2002 | Canne et al. | 530/324 |
| 2008/0227092 A1 * | 9/2008 | Lohse et al. | 435/6 |
| 2012/0220721 A1 * | 8/2012 | Melnyk et al. | 525/54.1 |

FOREIGN PATENT DOCUMENTS

| FR | 2 952 058 | 5/2011 | |
|---|---|---|---|
| WO | 96/34878 | 11/1996 | |
| WO | 98/28434 | 7/1998 | |
| WO | 01/68565 | 9/2001 | |
| WO | 01/87920 | 11/2001 | |
| WO | 2007/037812 | 4/2007 | |
| WO | 2011/058188 | 5/2011 | |
| WO | WO 2011/051906 | * 5/2011 | |

OTHER PUBLICATIONS

Canne et al., "Chemical Protein Synthesis by Solid Phase Ligation of Unprotected Peptide Segments", J. Am. Chem. Soc., 1999, vol. 121, pp. 8720-8727.
Dheur et al., "Synthesis of Peptide Alkylthioesters Using the Intramolecular N, S-Acyl Shift Properties of Bis(2-sulfanylethyl)amido Peptides", The Journal of Organic Chemistry, 2011, vol. 76, pp. 3194-3202.
Dommerholt et al., "Readily Accessible Bicyclononynes for Bioorthogonal Labeling and Three-Dimensional Imaging of Living Cells", Angew. Chem. Int. Ed., 2010, vol. 49, pp. 9422-9425.
Hou et al., "Peptidyl N,N-Bis(2-mercaptoethyl)-amides as Thioester Precursors for Native Chemical Ligation", Organic Letters, 2011, vol. 13, No. 3, pp. 386-389.
Johnson et al., "Total Chemical Synthesis, Folding, and Assay of a Small Protein on a Water-Compatible Solid Support", Angewandte Chemie, 2006, vol. 45, pp. 3283-3287.
Koning et al., "Synthesis of Peptide-PNA-Peptide Conjugates by Semi-Solid-Phase Chemical Ligation Combined with Deactivation/ Capture of Excess Reactants", Eur. J. Org. Chem., 2004, pp. 850-857.
Ollivier et al., "Bis(2-sulfanylethyl)amino Native Petide Ligation", Organic Letters, 2010, vol. 12, No. 22, pp. 5238-5241.
Villain et al., "Covalent capture: a new tool for the purification of synthetic and recombinant polypeptides", Chemistry & Biology, 2001, vol. 8, pp. 673-679.
International Search Report dated Jan. 16, 2013 in corresponding PCT application.

* cited by examiner

*Primary Examiner* — Karlheinz R Skowronek
*Assistant Examiner* — Sergio Coffa
(74) *Attorney, Agent, or Firm* — Young & Thompson

(57) ABSTRACT

Method for assembling proteins from peptide fragments. It allows the production of proteins in a manner that is simple, reliable and applicable on an industrial scale. This method allows the production of proteins of therapeutic or diagnostic interest. The invention also relates to kits for applying this synthesis method as well as test and/or diagnostic kits.

10 Claims, 15 Drawing Sheets

METHOD FOR SYNTHESIZING PROTEINS

FIELD OF THE INVENTION

Figure 1:
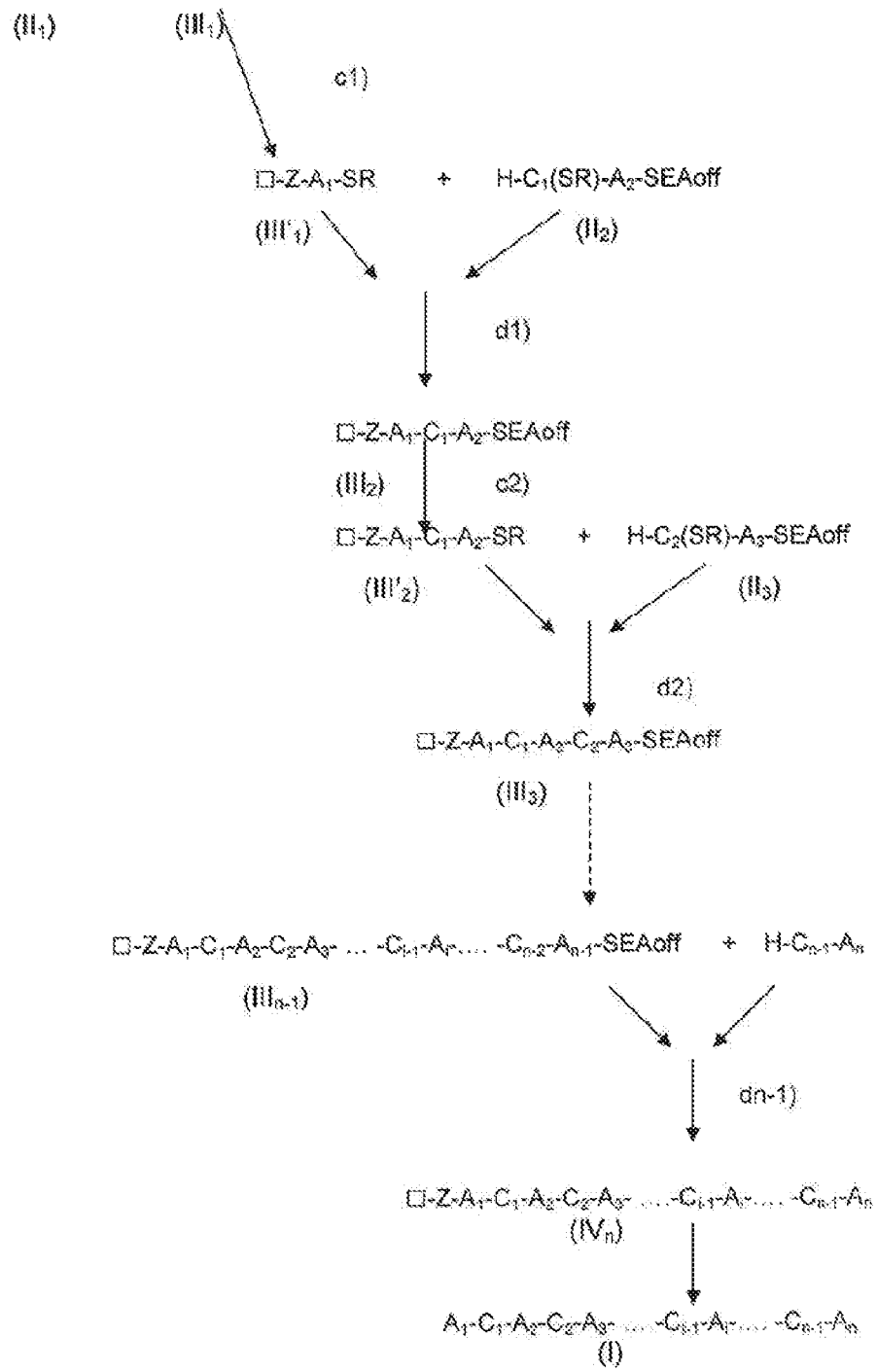

The present invention relates to a novel method for assembling proteins from peptide fragments. It allows proteins to be produced in a manner that is simple, reliable, can be automated and is applicable on an industrial scale. This method can be used for producing proteins of therapeutic or diagnostic interest. The invention also relates to kits and automated devices for applying this synthesis method as well as test and/or diagnostic kits.

TECHNOLOGICAL BACKGROUND

The synthesis of polypeptides by conventional methods in the solid phase, amino acid by amino acid, is limited by low yields when the polypeptides synthesized are large. Assembling two polypeptides by chemical ligation to produce a longer polypeptide is a known way of overcoming this limitation.

The complete synthesis of polypeptides is being used increasingly for preparing proteins with well-defined structures or bearing natural modifications, such as post-translational modifications, or non-natural modifications. The methods of chemical ligation provide an answer to this need, but they prove to be limited in their use and their industrial application.

In general, in these methods it is desirable for the bond between the polypeptides assembled by ligation to be native, i.e. to correspond to the natural structure of the polypeptides.

At present the main method for native ligation is that of Kent and Dawson, described for example in international applications WO 96/34878 and WO 98/28434. This method is based on a chemoselective reaction between a (C-terminal) thioester peptide and a cysteinyl-peptide. However, the main drawback of this method is production of the thioester peptides, which requires complex chemical methods. These methods cannot prevent competition between the reactions of the different thioesters, which inevitably leads to mixtures that may be difficult to separate, and therefore affecting the purity of the end product obtained, and to inevitable losses of yield.

An alternative method is the so-called Staudinger ligation, described in international applications WO 01/68565 and WO 01/87920. This comprises reaction of a phosphinothioester with an azide and hydrolysis of the combined reactants to form an amide bond. However, this method is difficult to apply on an industrial scale.

Another method, described in international application WO 2007/037812, is based on the reaction of an α-keto acid with an N-alkoxyamine in a decarboxylative condensation reaction. However, the keto acids are molecules that are difficult to manufacture and to incorporate in peptides. Thus, this third method is difficult to apply in peptide synthesis laboratories that do not possess means for carrying out complex organic syntheses.

The work by O. Melnyk et al., Org. Lett., 12(22), 5238-41 (2010) and application FR-2952058, as well as the work by Hou, W., Zhang, X., Li, F. and Liu, C. F. Peptidyl N,N-Bis(2-mercaptoethyl)-amides as Thioester Precursors for Native Chemical Ligation. Org. Lett. 13, 386-389 (2011), describe the native ligation of peptides by means of peptide-bis(sulphanylethyl)amino fragments. However, this method has never been used, to date, for the synthesis of peptides by assembling 3 or more fragments.

Application WO2011/058188 describes a purification technique consisting of introducing, at the end of solid-phase peptide synthesis, an N-terminal linkage provided with an azide function. Using a Staudinger-Bertozzi reaction or a cycloaddition (CuAAC, SPAAC), it is possible to graft the target peptide on a hydro-compatible resin functionalized beforehand with a phosphine or an alkyne. The peptide is finally released by cleavage of the linkage under mild conditions (base, nucleophilic, or photoirradiation) after washing the resin to remove the truncated peptides that had been unable to bind covalently with the resin. However, it is not envisaged at all in this document to use the grafting means for carrying out the synthesis of proteins by successive ligation of peptides.

The article by M. Villain et al., Chemistry and Biology 8 (2001) 673-679 describes a purification technique comprising a step in which the peptide comprising a cysteine or a threonine at the N-terminal end is grafted onto a resin, at the end of peptide synthesis, by reaction of the N-terminal residue with an aldehyde function, so as to form a thiazolidine or oxazolidine ring. The grafted peptide is then washed and then detached from the resin. However, it is not envisaged at all in this document to use the grafting means for carrying out the synthesis of proteins by successive ligation of peptides.

The documents U.S. Pat. No. 7,884,182 and Synthesis of Peptide-PNA-Peptide Conjugates by Semi-Solid-Phase Chemical Ligation Combined with Deactivation/Capture of Excess Reactants, Martijn C. de Koning. Eur. J. Org. Chem. 2004, 850-857, describe ligation of peptides using a solid support. The authors attach an H-Cys-A-SR peptide (R=alkyl) onto this support by the formation of a thiazolidine bond, then carry out a native ligation NCL between the supported thioester function and an H-Cys-B peptide. The H-Cys-A-SR peptides are difficult to synthesize. This method has a high risk of the occurrence of a polymerization or cyclization reaction during formation of the thiazolidine, since the two ends are reactive. Finally, this method does not allow more than one ligation to be carried out on the support.

Document FR 2 952 058 describes a method of ligation of peptides in the liquid phase, in the C-terminal to N-terminal direction. This method involves:
 the use of a SEA peptide,
 optionally the use of a SEAoff peptide, which is then converted to SEA.

Document US 2002/0132975 describes a method of assembling peptides by sequential native ligation of peptide fragments in the solid phase. The synthesis can be performed from the N-terminal end to the C-terminal end or in the opposite direction. It is based on:
 the use of peptides bearing an N-terminal cysteine and a C-terminal COS- group,
 conversion of the -COS- function to -COSR thioester at the C-terminal end of the resin-supported peptide,
 the use of the C-terminal thioester functionality of the resin-supported peptide for carrying out each ligation on the terminal cysteine of the next peptide fragment. However, the thioacid peptides (i.e. bearing the COS- function), such as those described as starting products in application US 2002/0132975, are difficult to prepare by synthesis, difficult to purify, and they are unstable. Moreover, the step of activation of the thioacid function to thioester is difficult especially when there are free cysteines in the peptide sequence, since there is a risk of alkylating the cysteines as well. Finally, the thioacid group, in contrast to the SEAoff group, is a reactive group that is not blocked. This is in particular illustrated in the work by Canne, L. E. et al., J. Am. Chem. Soc.

1999, 121, 8720-8727, in which the authors found significant formation of a cyclic by-product resulting from the residual reactivity of the thioacid group.

Relative to the methods of the prior art, the method of the invention has the benefit of greater efficacy of conversion of the SEAoff function to thioester, the reaction conditions are milder and they do not lead to the formation of by-products. Moreover, SEAoff is a system that is blocked under the ligation conditions, in contrast to other reactive groups, and in particular the thioacid described in application US 2002/0132975. Finally, the SEAoff segments are synthesized easily in the solid phase by the Fmoc/tert-butyl strategy, which is not the case with the thioacid peptides.

The adaptation of methods making it possible to implement peptide syntheses by complete synthesis on an industrial scale is a need that requires finding methods that are simple, inexpensive, and produce quality products of high purity, and are acceptable in terms of industrial hygiene.

For the reasons stated above, it has become essential to find a method of complete synthesis that is convergent and capable of industrial application, making it possible to synthesize a peptide chain of the desired length and nature; in particular, a method involving assembly from the N-terminal to the C-terminal, which offers qualities of simplicity of execution and purity of the peptides or polypeptides obtained. In fact, assembly from the N-terminal to the C-terminal offers a considerable advantage, compared to the far more conventional opposite strategy of assembly from the C-terminal to the N-terminal, as in this case the method allows "self-purification" of the peptide fragments by removing the acetylated N-truncated peptides, major impurities in solid-phase peptide synthesis (SPPS).

The present invention makes it possible to overcome the difficulties associated with multiple ligations in solution. It makes it possible to synthesize very large proteins. It can easily be automated and extrapolated to the industrial scale.

DESCRIPTION OF THE INVENTION

It was found, which forms the subject of the present invention, that the assembly of multiple peptide fragments in a method of solid-phase synthesis involving simple methods such as the formation of peptides-thioesters and native ligation, could lead to a method of complete synthesis that is convergent, can be automated, can be applied industrially and that meets the required criteria of purity.

For this purpose, the present invention proposes a method of assembling peptide fragments for manufacturing a polypeptide comprising n peptide fragments and at least n−1 amino acids bearing a thiol function, represented by the formula:

$$A_1\text{-}C_1\text{-}A_2\text{-}C_2\text{-}A_3\text{-} \ldots \text{-}C_{i-1}\text{-}A_i\text{-} \ldots \text{-}C_{n-1}\text{-}A_n \quad (I)$$

in which $A_1, A_2, A_3, \ldots A_i, \ldots, A_n$ are peptide fragments, $C_1, C_2, C_3 \ldots C_{i-1} \ldots C_{n-1}$ are amino acid residues bearing a thiol function,
n is comprised between 3 and 50,
preferably between 3 and 20,
or more preferably between 3 and 10, and
i is any integer between 2 and n.

This method involves:

(a1) at least one step of preparing a fragment Y-$A_1$-SEAoff ($II_1$) in which $A_1$ represents a peptide fragment the C-terminal of which bears a cyclic bis(2-sulphanylethyl)amino group

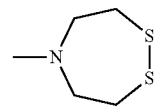

called SEAoff, and
Y is a fragment capable of reacting with a function of a solid support so as to form a bond between $A_1$ and a solid support, (b) at least one step of reaction of Y-$A_1$-SEAoff ($II_1$) with a solid support designated □-Y', □ representing the solid support itself and Y' representing a reactive function capable of reacting with Y in order to form a group Z according to the diagram:

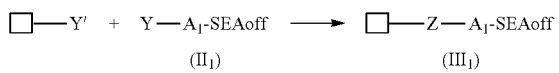

(a2) at least one step of preparing a fragment H-$C_1$($PG_1$)-$A_2$-SEAoff ($II_2$) in which $C_1$, $A_2$ and SEAoff are as defined above and ($PG_1$) represents H or a protective group of the thiol of the amino acid $C_1$, (c1) at least one step of preparing a thioester peptide of formula ($III_1'$) from the bis(2-sulphanylethyl)amino peptide □-Z-$A_1$SEAoff ($III_1$) according to the diagram:

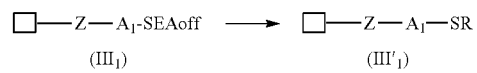

by the action of a thiol R-SH, optionally in the presence of a reducing agent of the cyclic disulphides, where R can be an alkyl or aryl radical, optionally substituted, (d1) at least one step of condensation of ($III_1'$) with the peptide fragment ($II_2$) in the presence of an aromatic thiol ArSH under conditions in which $PG_1$ is eliminated when it is different from H:

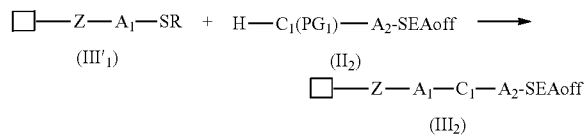

(an−1) at least one step of preparing a fragment $C_{n-1}$($PG_{n-1}$)-$A_n$ where ($PG_{n-1}$) represents H or a protective group of the thiol of the amino acid $C_{n-1}$, (dn−1) at least one step of condensation of $C_{n-1}$($PG_{n-1}$)-$A_n$ with

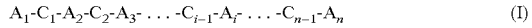
□-Z-$A_1$-$C_1$-$A_2$- … $C_{i-1}A_i$- … $C_{n-2}A_{n-1}$SEAoff ($III_{n-1}$)

in the presence of an aromatic thiol ArSH under conditions in which $PG_{n-1}$ is eliminated when it is different from H, in order to give:

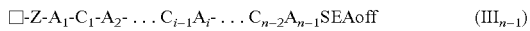
□-Z-$A_1$-$C_1$-$A_2$- … $C_{i-1}A_i$- … $C_{n-1}A_n$ ($IV_n$)

According to a particular embodiment of the invention, the method further comprises:

(e) a step of detaching the peptide $A_1$-$C_1$-$A_2$- … $C_{i-1}A_i$- … $C_{n-1}A_n$ (I) from the solid support.

According to an embodiment of the invention, the solid support □ is selected from resins, in particular from resins based on polystyrene, polyacrylamide, polyethylene glycol, cellulose, polyethylene, polyester, latex, polyamide, polydimethylacrylamide, synthetic or natural hydrophilic polymers, glass beads, silica gels.

According to an embodiment of the invention, $C_1, \ldots C_i \ldots C_n$ are cysteines.

According to an embodiment of the invention, $PG_1, \ldots PG_i \ldots PG_n$ are tert-butyl sulphenyl groups.

According to an embodiment of the invention,

Y' comprises a function selected from an azide, and Y is selected from the groups comprising an alkyne function, or Y' comprises an alkyne function and Y is selected from the groups comprising an azide function, or Y' comprises an aldehyde function, Y is H and the N-terminal amino acid of $A_1$ is selected from a cysteine, a serine or a threonine, or Y' comprises an aldehyde function, and Y comprises an $NH_2$ group capable of forming a Schiff base.

According to an embodiment of the invention, R is selected from an alkyl radical comprising 1 to 12 carbon atoms, linear or branched, optionally substituted, C6-C12 aralkyl or aryl, optionally substituted.

According to an embodiment of the invention, for every $i=2, \ldots n-2$, the method comprises (ci) at least one step of conversion of

$$\square\text{-}Z\text{-}A_1\text{-}C_1\text{-}\ldots C_{i-1}A_i\text{SEAoff} \qquad (III_i)$$

to

$$\square\text{-}Z\text{-}A_1\text{-}C_1\text{-}\ldots C_{i-1}A_i\text{-}SR \qquad (III'_i)$$

by the action of a thiol R-SH, optionally in the presence of a reducing agent of the cyclic disulphides, (di) at least one step of condensation of $C_i(PG_i)A_{i+1}\text{SEAoff}$ where $(PG_i)$ represents H or a protective group of the thiol of the amino acid $C_i$, with

$$\square\text{-}Z\text{-}A_1\text{-}C_1\text{-}\ldots C_{i-1}A_i\text{-}SR \qquad (III'_i)$$

in order to give

$$\square\text{-}Z\text{-}A_1\text{-}C_1\text{-}\ldots C_iA_{i+1}\text{SEAoff} \qquad (III_{i+1})$$

According to an embodiment of the invention, for every $i=2, \ldots n-2$, the steps di) of the method are carried out under conditions in which $PG_i$ is removed selectively in situ, without affecting SEAoff and the solvent of the reaction is an aqueous buffer, with pH between 4 and 9, containing an aromatic thiol.

Another subject of the invention is a solid support grafted with a peptide and corresponding to formula $(III_1)$ below:

$$\square\text{-}Z\text{-}A_1\text{-}\text{SEAoff} \qquad (III_1)$$

in which $A_1$ represents a peptide fragment, the C-terminal of which bears a cyclic bis(2-sulphanylethyl)amino group

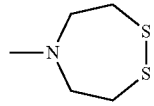

called SEAoff, $\square$ represents a solid support and Z represents a linkage group between $A_1$ and $\square$.

Such a solid support can be used in a polypeptide synthesis kit. Such a polypeptide synthesis kit usually comprises at least one support provided with at least one receiving zone, on or in which at least one grafted solid support $(III_1)$ is placed.

Another subject of the invention is an automated device for peptide synthesis that allows automated implementation of the synthesis method of the invention. Such a device comprises at least one reservoir in which a solid support grafted with a peptide and corresponding to the following formula $(III_1)$ is placed:

$$\square\text{-}Z\text{-}A_1\text{-}\text{SEAoff} \qquad (III_1)$$

It also comprises separate reservoirs containing:

peptides (IIi) $C_i(PG_i)A_{i+1}\text{SEAoff}$, which were described above, as well as:

at least one thiol R-SH, and optionally a reducing agent of the cyclic disulphides the coupling activators and the washing products.

Such an automated device of this kind also comprises mechanical means for taking and distributing samples of products, as well as data processing means allowing controlled application of these mechanical means.

Another subject of the invention is a solid support grafted with a polypeptide comprising n peptide fragments and at least n−1 amino acids bearing a thiol function and corresponding to formula $(IV_n)$ below:

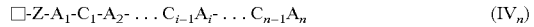

$$\square\text{-}Z\text{-}A_1\text{-}C_1\text{-}A_2\text{-}\ldots C_{i-1}A_i\text{-}\ldots C_{n-1}A_n \qquad (IV_n)$$

Such a solid support can be used for carrying out affinity tests between a polypeptide and another molecule.

For using these grafted solid supports in biological affinity tests, it is generally desirable for the peptide chain $A_1\text{-}C_1\text{-}A_2\text{-}\ldots C_{i-1}A_i\text{-}\ldots C_{n-1}A_n$ to be folded, so as to have a biologically relevant native conformation. For this, the chain is folded after the synthesis step, under conditions in which generally the cysteines are paired in order to form disulphide bridges.

Yet another subject of the invention is a biological test kit comprising at least one support provided with at least one receiving zone, on or in which at least one solid support grafted with at least one polypeptide comprising n peptide fragments and n−1 amino acids bearing a thiol function is placed, and corresponding to formula $(IV_n)$ below:

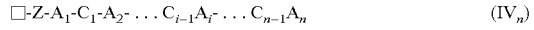

$$\square\text{-}Z\text{-}A_1\text{-}C_1\text{-}A_2\text{-}\ldots C_{i-1}A_i\text{-}\ldots C_{n-1}A_n \qquad (IV_n)$$

Yet another subject of the invention is a method of manufacturing a medicinal product comprising at least:

manufacturing at least one polypeptide by the method defined above, and combining it with a pharmaceutically acceptable support.

DESCRIPTION OF EMBODIMENTS OF THE INVENTION

The invention is now described in more detail and non limitatively in the following description.

By "peptides or polypeptide" is meant, in the context of the present application, a linear chain of amino acid residues (greater than or equal to two in number) joined together by peptide bonds. The "peptides or polypeptides" in the sense of the present application can therefore for example be oligopeptides, peptides or proteins according to the conventional acceptance of these terms. The amino acid residues present in the polypeptides according to the invention can be selected from amino acid residues that are or are not proteinogenic. Preferably, they are selected from the twenty proteinogenic amino acid residues.

The notation of the polypeptides proceeds from the N-terminal end to the C-terminal end. The amino acid residues present along the polypeptide chain are designated according to the usual one-letter or three-letter code. An amino acid residue is a polypeptide fragment of formula —NH—(CH—R)—(C=O)—, in which R represents a side chain, different from one amino acid to another.

By "peptide fragment" is meant, in the context of the present application, a portion of polypeptide comprising at least one amino acid residue. A peptide fragment, in the sense of the present application, can therefore be for example: a sequence of amino acid residues (such as -AHG- or -Ala-His-Gly-) if the peptide fragment comprises neither the N-terminal end nor the C-terminal end of the polypeptide; or else a sequence of amino acid residues having a group at its N-terminal end (such as H-AHG- or H-Ala-His-Gly-) if the peptide fragment comprises the N-terminal end of the polypeptide; or else a sequence of amino acid residues having a group at its C-terminal end (such as -AHG—OH or -Ala-His-Gly—OH) if the peptide fragment comprises the C-terminal end of the polypeptide.

It is understood that each of the peptide fragments preferably comprises only amino acid residues selected from the 20 proteinogenic amino acid residues. However, according to a particular embodiment, the peptide fragments $A_i$ in an internal position of the sequence can also comprise one or more non-proteinogenic amino acid residues, and one or more of the peptide fragments $A_2 \ldots A_i \ldots A_{n-1}$ can bear one or more modified amino acids, the modification being carried out before the method is implemented. As a non limitative example, the modification of the amino acids can in particular be selected from radicals selected from residues of carboxylic acids (biotin, acetyl group, aminooxyacetic residue, a fluorophore such as tetramethylrhodamine, a chelating agent of metals such as 1,4,7,10-tetraazacyclododecane-1,4,7,10-tetraacetic acid (DOTA), a lipid such as palmitic acid, a polymer, for example alpha-methoxy-omega-carboxy poly(ethylene glycol) or others. It can also be selected from post-translational modifications of proteinogenic amino acids known to a person skilled in the art (methylation, phosphorylation, acetylation, glycosylation, sulphation, hydroxylation, carboxymethylation, bearing suitable protective groups for incorporation in the solid phase, etc.), or optionally a medicinal product (the protein then serving as vector).

The presence of modified amino acids in particular allows the polypeptide to be functionalized with a view to detecting interactions of the polypeptide with other molecules (fluorescence markers etc.), but other types of functionalization can be provided.

In a simple way, a modification can be introduced by using a non-proteinogenic amino acid, in particular a derivative of proteinogenic amino acid, to introduce the modification during the solid-phase synthesis of the fragment in question. By way of example, it is possible to use an Fmoc-L-Lys(biotin)—OH, i.e. a lysine bearing a biotin on its side chain, in order to carry out the synthesis of a fragment. This fragment is then used in the assembly identically to that which uses fragments of proteinogenic amino acids.

The amino acid residues of the polypeptides $A_1, \ldots A_i, A_n$ can optionally be protected temporarily or permanently by protective groups of the functions carried by the side chains, the nature of which varies depending on the reactive functions of the side chains, which are well known to a person skilled in the art.

According to an embodiment of the invention, a peptide fragment $A_i$ comprises between 2 and 600 amino acid residues, preferably between 5 and 100 amino acid residues, more especially preferably between 8 and 50 amino acid residues.

The polypeptide of formula (II) can be obtained for example by a usual method of peptide synthesis, in particular a method of solid-phase synthesis. It can also be obtained by means of a previous native ligation.

The preparation of bis(2-sulphanylethyl)amino peptide: Y-$A_1$-SEAoff (step a1) of the method) can be carried out by the method described by Melnyk, O. et al., Bis(2-sulphanylethyl)amino native peptide ligation., Org. Lett., 12(22), 5238-41(2010), as well as in FR-2952058. According to the embodiment of this method, the C-terminal amino acid is coupled to a support of polymer resin P grafted with SEA (bis(2-sulphanylethyl)amino) by bringing a support of SEA grafted polymer resin into contact with a halide of amino acid or with an amino acid and an activating agent, preferably selected from PyBOP® (benzotriazol-1-yl-oxytripyrrolidinophosphonium hexafluorophosphate), BOP, PyBroP® (bromo-tris-pyrrolidino-phosphonium hexafluorophosphate), or else HATU (2-(1H-7-azabenzotriazol-1-yl)-1,1,3,3-tetramethyluronium hexafluorophosphate methanaminium) and more especially preferably PyBroP and HATU. This embodiment is described in more detail below in the examples of the preparation of the starting peptide fragments. $A_1$-SEA-P is then functionalized with a group Y and then detached from the polymer P.

The method of the invention comprises the reaction of a functionalized peptide Y-$A_1$-SEAoff ($II_1$) with a solid support designated □-Y', □ representing the solid support itself and Y' representing a reactive function capable of reacting with Y to form a group Z according to diagram 1:

Diagram 1

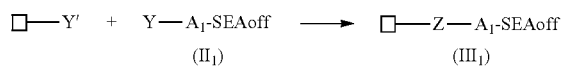

The solid support is preferably a polymer in the form of insoluble or soluble particles (beads). It is possible for example to use resins based on polystyrene, polyacrylamide, polyethylene glycol, cellulose, polyethylene, polyester, latex, polyamide, polydimethylacrylamide and resins derived therefrom. It is also possible to use a silica gel or glass beads as the solid support.

Advantageously, a solid support is used selected from the synthetic hydrophilic polymers such as the resins PEGA, ChemMatrix®, SPOCC (superpermeable organic combinatorial chemistry) or natural carbohydrate polymers such as agarose or sepharose.

These resins are grafted with a group Y' comprising a function selected from an azide, an alkyne, preferably a true alkyne or terminal alkyne, a cyclooctyne, Y is then itself selected from an alkyne, preferably a true alkyne or terminal alkyne, and an azide.

According to a variant, these resins are grafted with a group Y' that comprises an aldehyde function, Y is H and the N-terminal amino acid of $A_1$ is selected from a cysteine, a serine or a threonine, or an $NH_2$ group capable of forming a Schiff base, such as the hydrazinocarbonyl group H2NNHCO, or more generally a derivative of hydrazine or $H_2NO$, i.e. a derivative of hydroxylamine.

More precisely, the preferred embodiments of the invention have the following:

When Y' comprises an alkyne, Y comprises an azide,
When Y' comprises an azide, Y comprises an alkyne,
When Y' is an aldehyde, Y is H and the N-terminal amino acid of $A_1$ is selected from a cysteine, a serine or a threonine or
When Y' is an aldehyde, Y is an $NH_2$ group capable of forming a Schiff base, such as the hydrazinocarbonyl group H2NNHCO, or more generally a derivative of hydrazine or H$_2$NO, i.e. a derivative of hydroxylamine.

The bond between the peptide fragment and the solid support is effected by means of a suitable functional group, called a linker. Thus, firstly the N-terminal peptide fragment is fixed onto the functional groups that are linkers of the solid support (leaving the C-terminal end of the peptide fragment in the form of SEAoff) by means of the amino acid corresponding to the N-terminal end of the polypeptide to be synthesized, which constitutes the first primer, then the next peptide fragments are added according to the succession of reactions described below.

According to a first variant, the solid support grafted with the bis(2-sulphanylethyl)amino peptide: □-Z-A$_1$-SEAoff (III$_1$) can be prepared by the method described in WO2011/058188:

The peptide A$_1$-SEAoff is reacted with a compound corresponding to the general formula X$_1$-L-X$_2$, in which X$_1$ represents a group selected from:

—N$_3$
and
—C≡CH

L represents a spacer group and X$_2$ represents a group comprising a functional group capable of reacting with the terminal NH$_2$ group of the peptide A$_1$, the bond between X$_2$ and A$_1$ being resistant under the ligation conditions mentioned above and cleavable under conditions that do not degrade the peptide chain. Such groups X$_2$ are described in detail in WO2011/058188.

The peptide A1 is supported by a solid phase via its terminal acid function and a SEAoff precursor group. Bringing the supported peptide A$_1$ into contact with the compound X$_1$-L-X$_2$ results in the formation of a covalent bond between the terminal NH$_2$ group of the peptide A$_1$ and the group X$_2$ to form a compound X$_1$-L'-A$_1$ in which X$_1$ has the same meaning as above and L' represents a linker arm produced by the condensation of -L-X$_2$ with the N-terminal end of the peptide A$_1$. The SEAoff group is only formed after detaching the peptide X$_1$-L'-A$_1$ from the solid support.

Usually, L' is an alkane di-yl chain comprising from 1 to 50 carbon atoms, and one or more functions that can be selected, non limitatively, from: a hydroxyl function, an amine function, an ester function, a thioester function, an ether function, an amide function, an NO$_2$ function, an SO$_2$ function, a halogen atom, an optionally substituted aryl group, and this alkane di-yl chain is optionally interrupted by one or more groups selected from: an ether bridge (—O—), an amine bridge (—NH—), an ester bridge (—COO—), an amide bridge (—CONH—), a urea bridge (—NH—CO—NH—), a urethane bridge (—NH—CO—O—).

Next, the reactive group X$_1$ reacts with a solid support bearing a suitable functionality. Such supports are described in WO2011/058188. In particular, when X$_1$ represents:

—C≡CH a solid support bearing one of the following functionalities can be selected □-N$_3$
□—NH—CO—(CH$_2$)$_m$—N$_3$ When X$_1$ represents N$_3$, a solid support functionalized with an alkyne group can for example be selected, preferably a true alkyne, present in a more or less complex molecule such as those illustrated in WO2011/058188, for example:

□—NH—CO—(CH2)m—C≡C—H, a cyclooctyne group etc.

The reaction between X$_1$ and the solid support is carried out under chemoselective conditions and no competing reaction takes place between X$_1$ and the amino acids of the peptide A$_1$.

According to a second variant, the solid support grafted with the bis(2-sulphanylethyl)amino peptide: □-Z-A$_1$-SEAoff (III$_1$) can be prepared by the method described in M. Villain et al., Chemistry and Biology 8 (2001) 673-679.

According to this method, a thiazolidine or oxazolidine bond is formed between an aldehyde function borne by the solid support and a cysteine, respectively a serine or a threonine, N-terminal of the peptide A$_1$ according to the following diagram 2:

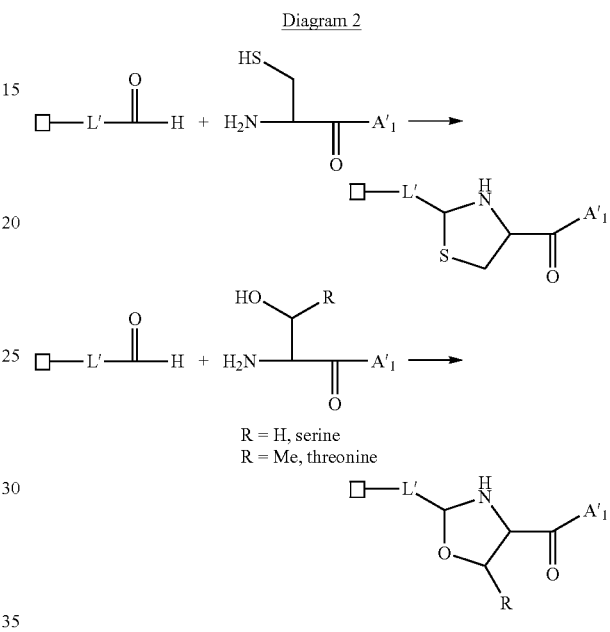

Diagram 2

In this diagram, L' represents a spacer arm between the solid support and the aldehyde function, A'$_1$ represents the peptide residue that forms with the N-terminal cysteine, serine or threonine of the peptide A$_1$. Advantageously, L' is an alkane di-yl chain comprising from 1 to 50 carbon atoms, and one or more functions that can be selected, non limitatively, from: a hydroxyl function, an amine function, an ester function, a thioester function, an ether function, an amide function, an NO$_2$ function, an SO$_2$ function, a halogen atom, an optionally substituted aryl group, and this alkane di-yl chain is optionally interrupted by one or more groups selected from: an ether bridge (—O—), an amine bridge (—NH—), an ester bridge (—COO—), an amide bridge (—CONH—), a urea bridge (—NH—CO—NH—), a urethane bridge (—NH—CO—O—).

In fact, according to this variant, grafting can be carried out by a direct reaction between a peptide and the functionalized solid support. The only requirement consists of the presence of a cysteine, serine or threonine residue in the N-terminal position of the peptide A$_1$. Either the desired final peptide comprises one of these amino acids in the N-terminal position, and the method can be carried out on this peptide without sequence modification; otherwise, it is necessary to provide the addition of one of these three residues in the N-terminal position of the target sequence.

In all cases, the linker arm Z joining the solid support and A1 together must be resistant under the conditions of execution of the steps of transformation ci) and of condensation di). Moreover it must be cleavable under conditions allowing the release of the polypeptide (I) without damaging it.

The invention is further based on the preparation of fragments H—$C_{i-1}(PG_{i-1})$-$A_i$-SEAoff ($II_i$) represented below (with i=2, ... n−1) in which $C_{i-1}$, $A_i$ and SEAoff are as defined above and ($PG_{i-1}$) represents H or a protective group of the thiol of the amino acid $C_{i-1}$.

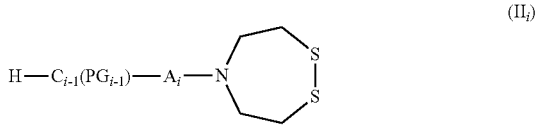

($II_i$)

The peptide of formula ($II_i$) comprises a hydrogen atom and a residue $C_{i-1}(PG_{i-1})$ at the N-terminal end. The residue $C_{i-1}$ is an amino acid residue comprising a thiol function. This thiol function can in particular be a beta-amino thiol function (in which case the residue $C_{i-1}$ preferably represents the cysteine residue), a gamma-amino thiol function (in which case the residue $C_{i-1}$ preferably represents the homocysteine residue), or a selenocysteine.

Throughout the following description, according to a particular embodiment, $C_{i-1}$ can be read as representing a cysteine residue (Cys).

According to a preferred variant of the invention, the thiol function of $C_{i-1}$ is protected by a protective group $PG_{i-1}$. Advantageously, $PG_{i-1}$ represents a protective group (SR') so as to form a disulphide residue on the thiol of the amino acid $C_{i-1}$, and R' represents a $C_1$-$C_6$ alkyl group, in particular SR' represents a tert-butyl sulphenyl group, or a $C_6$-$C_{12}$ aryl sulphenyl or aralkyl sulphenyl group, such as phenyl sulphenyl or benzyl sulphenyl.

It is understood that each peptide fragment $A_i$ can have been prepared beforehand by a succession of operations as described above, according to the method of the invention or by any other method of peptide synthesis.

The invention is in particular based on the transformation ci) of peptides grafted onto a solid support and bearing a SEAoff function of thioester peptides, □-Z-$A_1$-$C_1$-$A_2$- ... $C_{i-2}$-$A_{i-1}$—SR (I=2, ... n) ($III'_{i-1}$) and their condensation reaction di) with a peptide (or polypeptide) bearing a bis(2-sulphanylethyl)amino function in the cyclic disulphide state, corresponding to the general formula:

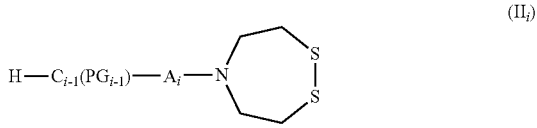

($II_i$)

in which $A_i$ represents a peptide fragment the C-terminal of which bears a cyclic bis(2-sulphanylethyl)amino group

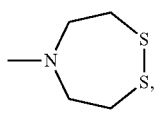

called SEAoff, and $C_{i-1}$ represents an amino acid residue bearing a thiol function.

It is understood that the term SEAoff denotes the unreactive cyclic disulphide, as opposed to the reactive disulphide of structure —N[$(CH_2)_2$—SH]$_2$, called SEAon hereinafter.

This particular step was described for application to other compounds in Dheur, J., Ollivier, N., Vallin, A. and Melnyk, O. Synthesis of Peptide Alkylthioesters Using the Intramolecular N,S-Acyl Shift Properties of Bis(2-sulfanylethyl) amido Peptides. J. Org. Chem. 76, 3194-3202 (2011).

This synthesis step is based on at least one step ci) (with I=2, ... n−1) of conversion of

  ($III_i$)

to

  ($III'_i$)

by the action of a thiol R-SH, optionally in the presence of a reducing agent of cyclic disulphides.

It is understood that when I=n, conversion of SEAoff to SR is not necessary and the condensation reaction dn) of ($III_{n-1}$) with the C-terminal peptide fragment -$C_{n-1}(PG_{n-1})A_n$ can be carried out directly.

This transformation is followed by a step of condensation di) of

  ($III'_i$)

with $C_i(PG_i)$-$A_{i+1}$-SEAoff ($II_{i+1}$) in the presence of an aromatic thiol ArSH under conditions in which $PG_i$, when it is different from H, is eliminated in order to give:

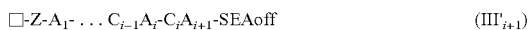  ($III'_{i+1}$)

In the case when i=n−1, the condensation step is carried out with a peptide -$C_{n-1}(PG_{n-1})A_n$ not bearing the SEA group, the conversion of SEAoff to SR is not necessary but can be carried out, in particular in the case when the whole synthesis is carried out using an automatic device, the rest of the operating conditions being the same as for the other condensations, in particular in the presence of an aromatic thiol ArSH under conditions in which $PG_{n-1}$, when it is different from H, is eliminated.

The alkyl radical represented by R is a linear or branched alkyl radical with 1 to 12 carbon atoms, or C6-C12 aryl optionally substituted with one or more groups selected from the halogen atoms (F for example), or the $CO_2H$, $SO_3H$, $CONH_2$, OH, SH, alkyloxy, alkylthio, mercaptoalkylthio radicals, the residue of an ester or a polyethylene glycol residue, or with an optionally substituted phenyl, or other organic groups that do not interfere with the reactions employed. The thiol of general formula R-SH used in step ci) can be for example $HSCH_2CH_2CO_2H$, $HSCH_2CH_2SO_3H$, $HSCH_2CH_2SH$, $HSCH_2CH_2SCH_2CH_2SH$ or $HSCH_2Ph$.

According to a variant, if the thiol R-SH is sufficiently reducing, the presence of an additional reducing agent of the cyclic disulphides is not necessary.

The aromatic thiol used in step di) is advantageously selected from reducing compounds of the disulphide bonds, preferably selected from thiophenol and/or the derivatives obtained by substitution of the aromatic ring, for example 4-carboxymethylthiophenol. Alternatively, non-aromatic thiols such as dithiothreitol, benzylmercaptan, can be used instead of the aromatic thiol. Of course, mixtures of these thiols may also be suitable.

The reducing agent of SEAoff used in step ci) can be selected from the reducing agents of cyclic disulphides. It can in particular be selected from the phosphines (for example tris (2-carboxyethyl)phosphine), or any other reducing agent of the cyclic disulphides such as the thiols (for example dithiothreitol (DTT)).

Advantageously, the condensation step is carried out in the presence of an excess of $C_i(PG_i)$-$A_{i+1}$-SEAoff or of $C_{n-1}(PG_{n-1})$-$A_n$.

The ligation reaction preferably takes place in an aqueous medium, for example in a phosphate buffer with a pH between 4 and 9. Preferably, this reaction is carried out at a pH between 5 and 9, advantageously between 5.5 and 8.5, more especially preferably at a pH between 5.5 and 7.5 and ideally at a pH close to 7.0.

The condensation reaction is preferably carried out at a temperature between 0 and 50° C., and ideally at a temperature of about 37° C. The duration of the reaction is adjusted depending on the choice of reagents and the other conditions of the reaction. The appropriate duration can also be adjusted according to the results of a liquid chromatography—mass spectrometry analysis during the reaction. The appropriate duration will typically be from a few hours to a few days.

Advantageously, washing the solid support is carried out between two condensation steps, so as to remove the unreacted excess peptide residues, which can optionally be recovered or recycled.

Optionally, deprotection of the side chains of the amino acids making up the polypeptide is carried out by means that are well known to a person skilled in the art.

According to the invention, the method of assembling multiple peptide fragments can be represented according to the diagram shown in FIG. 1.

According to the invention, the method leads to the preparation of a multiple peptide assembly grafted onto a solid support ☐ via a linkage group Z, the peptide assembly comprising amino acid residues bearing a thiol function, i.e. an assembly of n peptide fragments $A_i$ and of at least n−1 amino acids $C_i$ bearing a thiol function, represented by the formula:

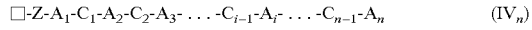
$$\square\text{-}Z\text{-}A_1\text{-}C_1\text{-}A_2\text{-}C_2\text{-}A_3\text{-}\ldots\text{-}C_{i-1}\text{-}A_i\text{-}\ldots\text{-}C_{n-1}\text{-}A_n \qquad (IV_n)$$

in which $A_1, A_2, A_3, \ldots A_i \ldots, A_n$ are peptide fragments, $C_1, C_2, C_3 \ldots C_{i-1} \ldots C_{n-1}$ are amino acid residues bearing a thiol function,
n is comprised between 3 and 50,
preferably between 3 and 20,
or more preferably between 3 and 10, and
i is any integer between 2 and n.

The method of the invention therefore comprises n−1 steps of peptide assembly. Advantageously the n−1 steps of peptide assembly are based on a step of conversion of ☐-Z-$A_1$-$C_1$-$A_2$-...$C_{i-1}A_i$-SEAoff to ☐-Z-$A_1$-$C_1$-$A_2$-...$C_{i-1}$-$A_i$—SR by the action of a thiol R-SH, optionally in the presence of a reducing agent of cyclic disulphides, followed by a step of condensation of ☐-Z-$A_1$-$C_1$-$A_2$- . . . $C_{i-1}A_i$—SR with $C_i(PG_i)$-$A_{i+1}$-SEAoff in the presence of an aromatic thiol ArSH under conditions in which $PG_i$ is eliminated in order to give: ☐-Z-$A_1$-$C_1$-$A_2$- . . . $C_{i-1}A_i$-$C_iA_{i+1}$-SEAoff.

However, it is not ruled out that one or more steps of peptide assembly employed in the synthesis of the peptide ($IV_n$) may be carried out using another ligation method known to a person skilled in the art.

In particular, as explained above, step n−1 can be an SEA ligation, by direct reaction of SEAoff with $C_{n-1}(PG_{n-1})$-$A_n$.

Advantageously, all the steps of the method of production of the peptide ($IV_n$) are carried out following the sequence of steps ci), di), i=1, . . . n−2, optionally cn−1), then dn−1).

In the manufacture of the polypeptide and preferably before detaching it from the resin, it is also possible to envisage one or more steps of chemical treatment, such as a conversion of amino acids, by methods that are known to a person skilled in the art, for example alkylation of a homocysteine to methionine or desulphurization of a cysteine or deselenization of a selenocysteine to alanine.

Preferably, the method is followed by a step of cleavage of the bond between the solid support and the peptide (I) under conditions allowing the peptide (I) to be released:

$$A_1\text{-}C_1\text{-}A_2\text{-}C_2\text{-}A_3\text{-} \ldots \text{-}C_{i-1}\text{-}A_i\text{-} \ldots \text{-}C_{n-1}\text{-}A_n \qquad (I)$$

The cleavage means will differ depending on the nature of the linker arm Z. In particular, following the teaching of WO2011/058188, it is possible, depending on the nature of the linker arm Z, to release the peptide (I) by cleavage of the covalent bond between part $X_2$ of the spacer arm Z and the peptide (I) by nucleophilic attack, or under alkaline or acid conditions or by UV irradiation.

When the spacer arm Z results from the condensation of a cysteine from a serine or an n-terminal threonine of the peptide $A_1$ with an aldehyde function carried by the solid support to form a thiazolidine, or respectively an oxazolidine, ring, the final peptide is advantageously released by treatment with O-methyl hydroxylamine, following the teaching of M. Villain et al., Chemistry and Biology 8 (2001) 673-679.

The latter conditions are also applicable to the case when the bond Z formed is a Schiff base.

Another subject of the invention is a solid support grafted with a peptide and corresponding to the following formula:

$$\square\text{-}Z\text{-}A_1\text{-SEAoff} \qquad (III_1)$$

in which Z, ☐, $A_1$ and SEAoff have the same meaning as above. Such supports, grafted with a first peptide fragment $A_1$, make it possible to initiate the synthesis of complex polypeptides. We may in particular envisage industrial or semi-industrial preparation of solid supports grafted with sequences of peptides $A_1$ of general interest, which are often used as the N-terminal sequence of peptides of biological interest. For example, we may mention the following types of sequences: signal peptides for addressing and secretion of proteins, marker peptides (of fluorescence for example), purification tags such as histidine tags, peptides bearing an ubiquitination signal etc.

Such a solid support of this kind, grafted with a first peptide, in particular a peptide of interest, can advantageously be used in a kit for polypeptide synthesis. In such a kit, it can be combined with a support comprising receiving zones, such as the wells of a multiwell plate in which successive ligation reactions can be carried out. It can be combined with synthesis reagents such as those described above for carrying out ligation reactions.

Another subject of the invention is an automated device for peptide synthesis that allows automated implementation of the synthesis method of the invention. Such a device comprises at least one reservoir in which a solid support grafted with a peptide and corresponding to formula ($III_1$) below is placed:

$$\square\text{-}Z\text{-}A_1\text{-SEAoff} \qquad (III_1)$$

$A_1$ can in particular be selected from the peptides of interest that were mentioned above.

It also comprises reservoirs containing:
peptides ($IIi$) $C_i(PG_i)A_{i+1}$SEAoff that were described above, different reservoirs being provided for containing each peptide with a different sequence.
Reservoirs are also provided for:
at least one thiol R-SH, and optionally a reducing agent of the cyclic disulphides,
the coupling activators and
the washing products.

An automated device of this kind also comprises mechanical means for taking samples from the different reservoirs and means for distributing these samples in the reservoir comprising the solid support. Said means can consist of a set of pipes for circulating fluids and valves, optionally arranged in microfluidic circuits, or in hinged arms equipped with sampling pipettes. The automated device also comprises data processing means (software) allowing controlled application of these mechanical means, allowing successive reactions to be carried out.

Another subject of the invention is a solid support grafted with a polypeptide comprising n peptide fragments $A_i$ and at least n−1 amino acids $C_i$ bearing a thiol function and corresponding to formula $(IV_n)$ below:

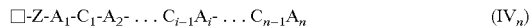

$$\square\text{-}Z\text{-}A_1\text{-}C_1\text{-}A_2\text{-}\ldots C_{i-1}\text{-}A_i\text{-}\ldots C_{n-1}\text{-}A_n \qquad (IV_n)$$

in which Z, $\square$, $A_i$, $C_i$, i, n and SEAoff have the same meaning as above. In fact, at the end of the successive ligations and optional deprotection of the side chains of the amino acids, and folding of the peptide chain, the solid support can be used for carrying out biological tests, in particular affinity tests of the polypeptides synthesized for molecules of any kind.

Another subject of the invention consists of an test and/or diagnostic kit comprising at least one support comprising at least one receiving zone, on which at least one solid support grafted with at least one polypeptide comprising n peptide fragments and at least n−1 amino acids bearing a thiol function is placed, the grafted solid support corresponding to formula $(IV_n)$ below:

$$\square\text{-}Z\text{-}A_1\text{-}C_1\text{-}A_2\text{-}\ldots C_{i-1}\text{-}A_i\text{-}\ldots C_{n-1}\text{-}A_n \qquad (IV_n)$$

Thus, the test kit can be used for screening biologically active molecules or for diagnostic tests. It can be envisaged that the diagnostic kit comprises several separate receiving zones, on which a solid support grafted with identical or different polypeptides is deposited. For example, solid supports grafted with identical or different polypeptides can be placed in the wells of a multiwell plate so as to form a test and/or diagnostic support.

Preferably, for carrying out tests, the polypeptides grafted onto the solid support are brought into contact beforehand with a medium that promotes the formation of a two- and/or three-dimensional structure. For example, following the teaching of E. C. B. Johnson et al., Angew. Chem. Int. Ed. 2006, 45, 3283-3287, the polypeptide can be put in contact with a phosphate buffer of pH 8 and can be subjected to the release of air, or the peptide can be put in contact with an aqueous solution with pH equal to 9. Another useful means for folding is the use of the pair GSH, GSSG (GSH for glutathione, GSSG for oxidized glutathione).

The test and/or diagnostic kit can further comprise means for detecting interaction between the polypeptides and the molecules tested.

Yet another subject of the invention is a method of manufacturing a medicinal product comprising at least:
manufacturing at least one polypeptide by the method defined above, and
combining it with a pharmaceutically acceptable support.

In fact, the method of the invention can be applied with the aim of synthesizing polypeptides having therapeutic activity, in particular vaccines. Combining them with a pharmaceutically acceptable support is carried out by a person skilled in the art based on his general knowledge and in relation to the properties of the polypeptide (in particular solubility) and the method of administration selected.

Other features and advantages of the invention will become apparent on reading the following description of a preferred embodiment of the invention, given as an example, and referring to the attached drawing.

FIGURES

FIG. 1: general diagrammatic representation of the method of peptide synthesis according to the invention.

Figure 2:
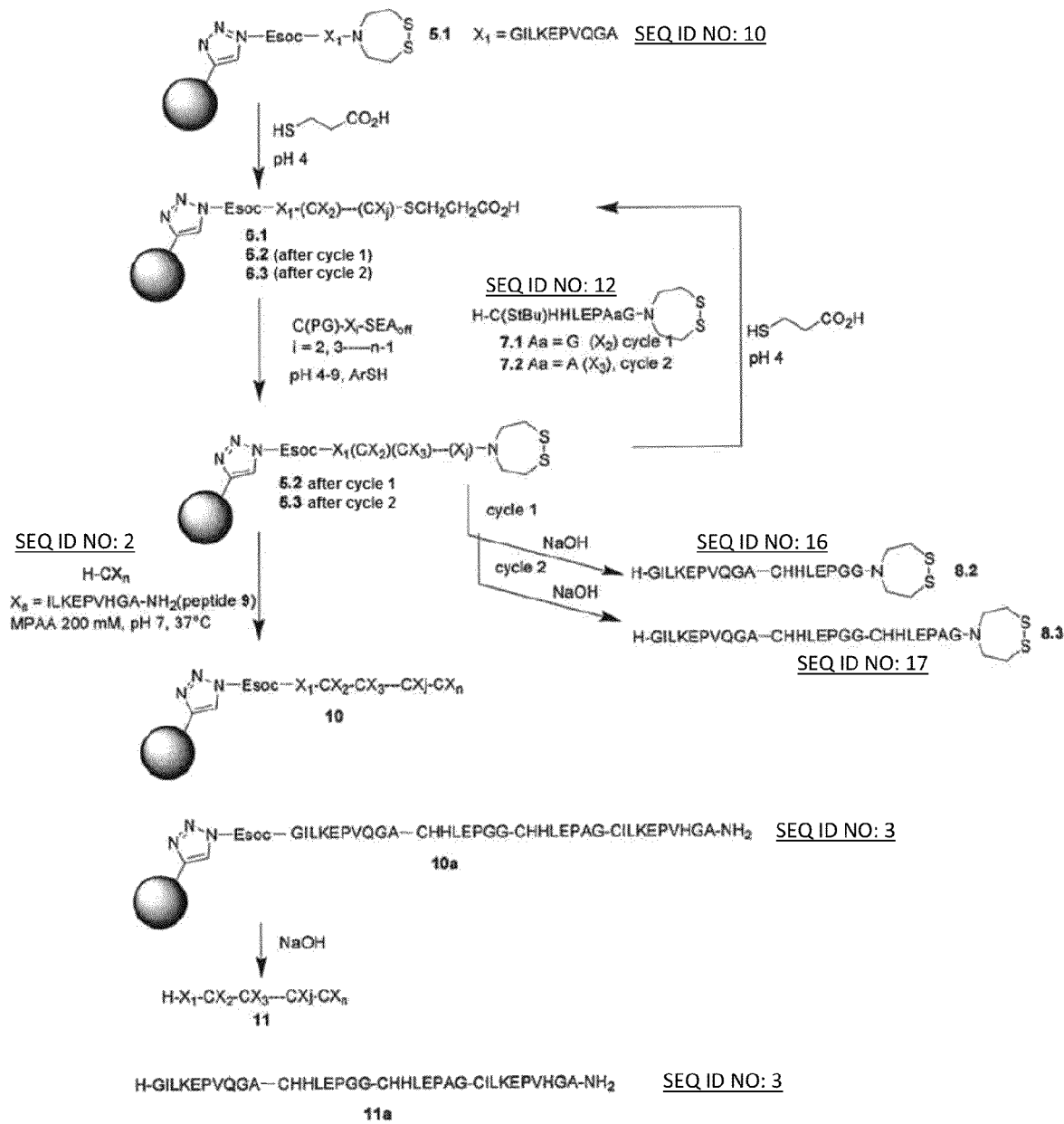

FIG. 2: diagrammatic representation of the synthesis method of the peptide 11a, H-GILKEPVQGA-CHHLEPGG-CHHLEPAG-CILKEPVHGA-NH₂ according to Example I.

Figure 3:
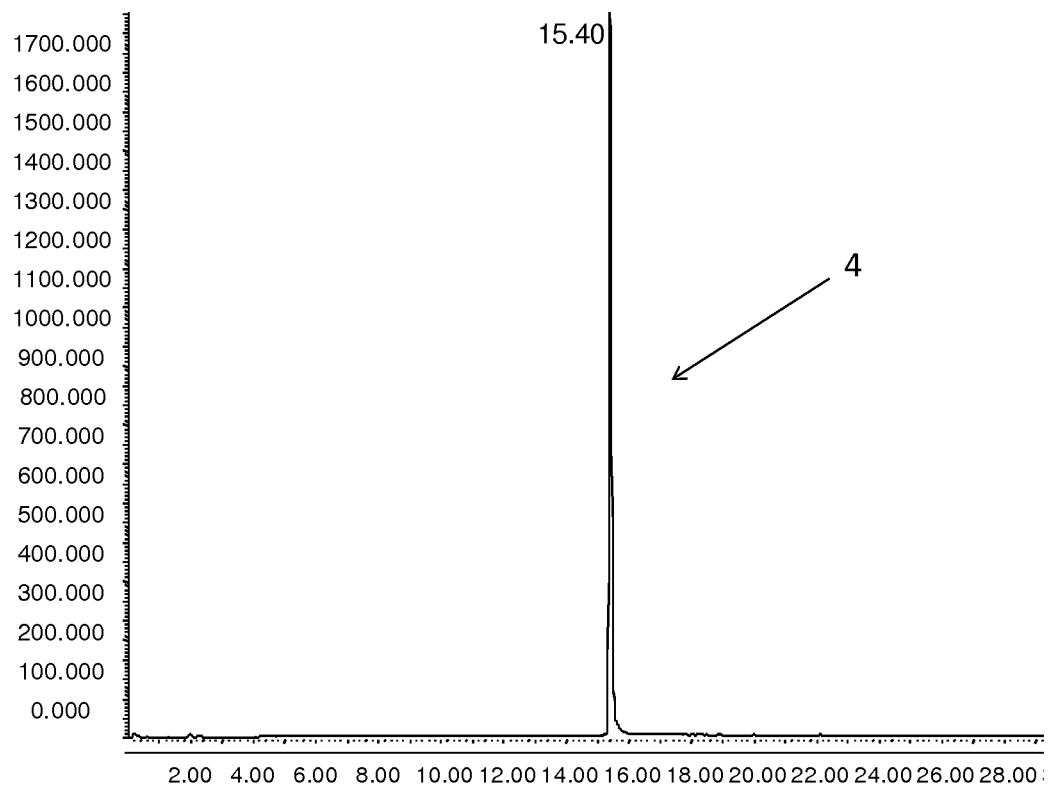
Figure 4:
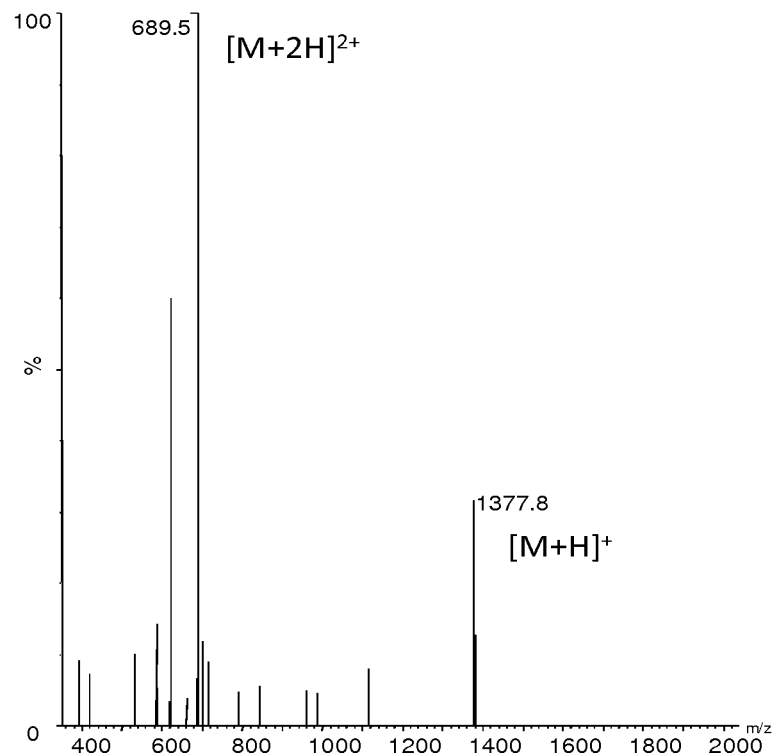
Figure 5:
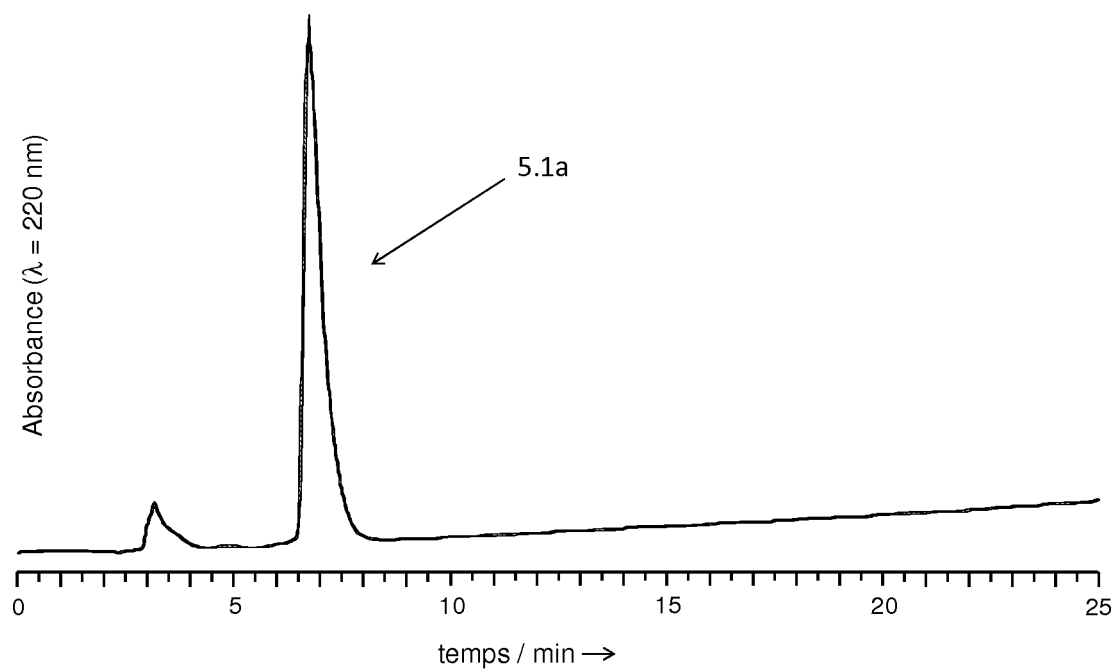
Figure 6:
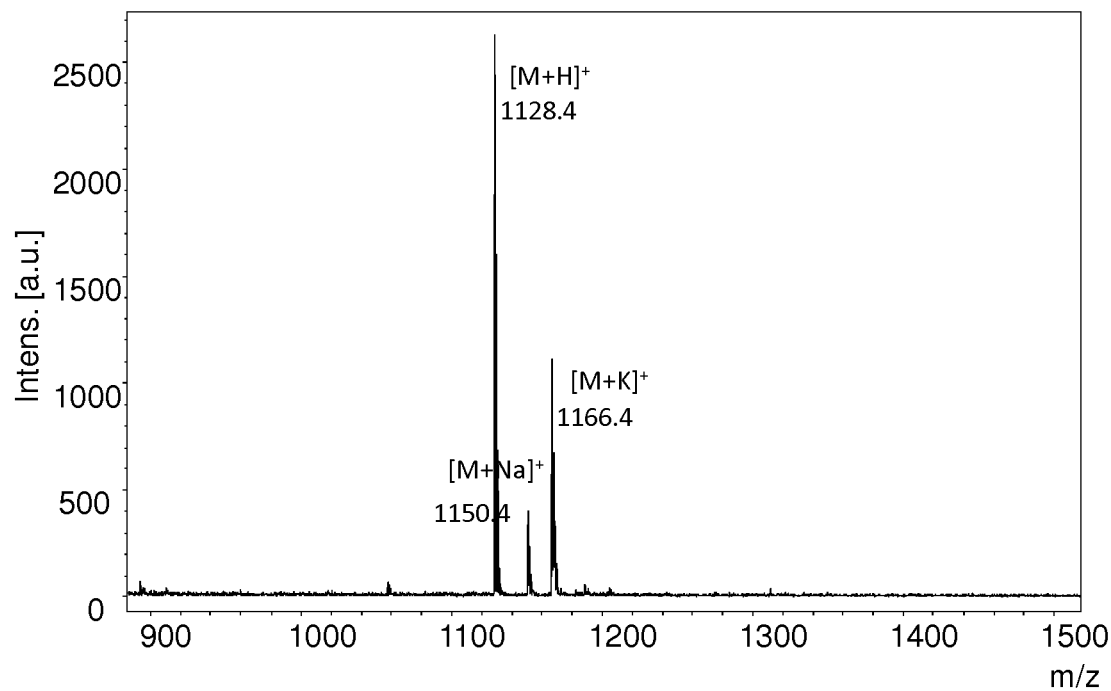
Figure 7:
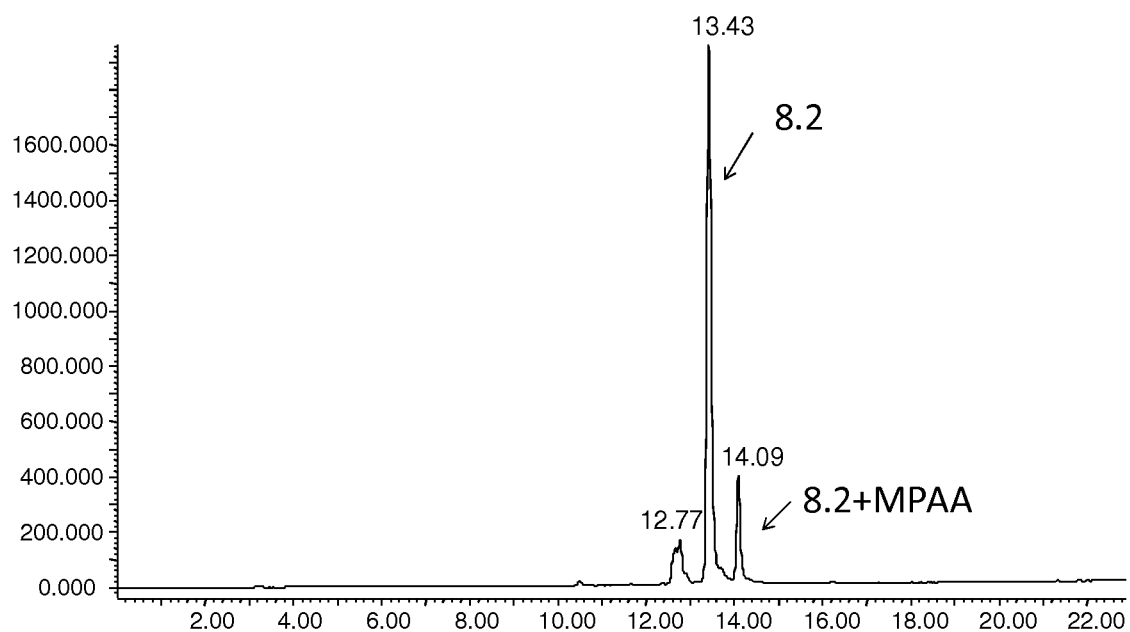
Figure 8:
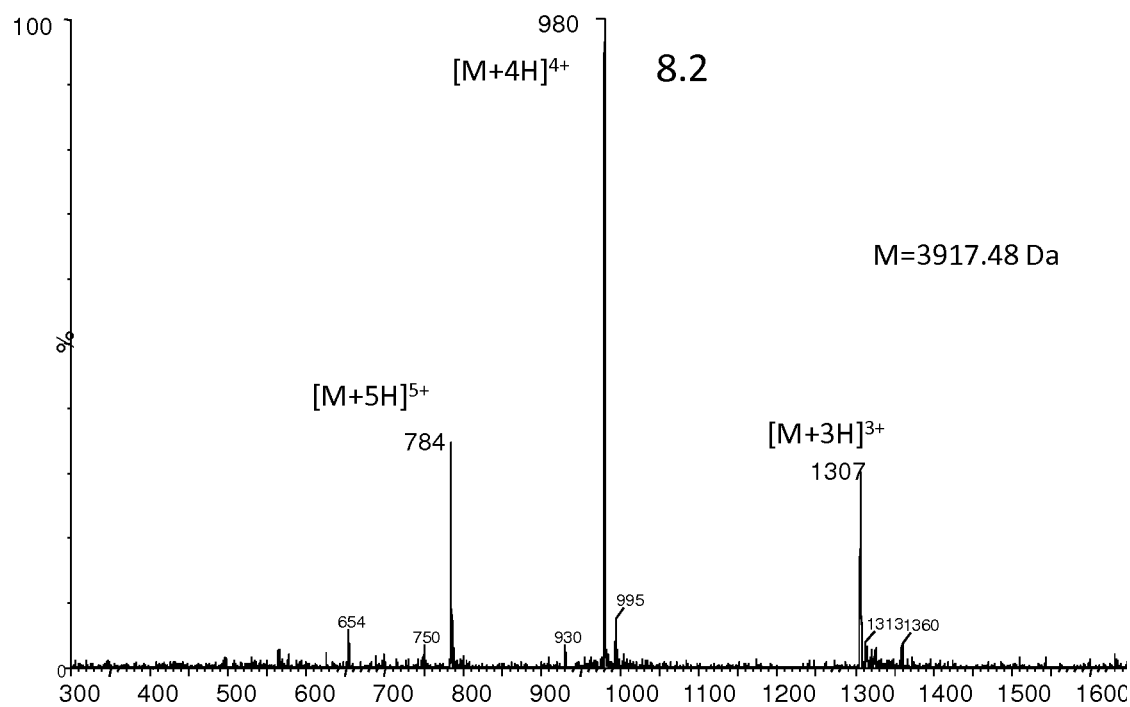
Figure 9:
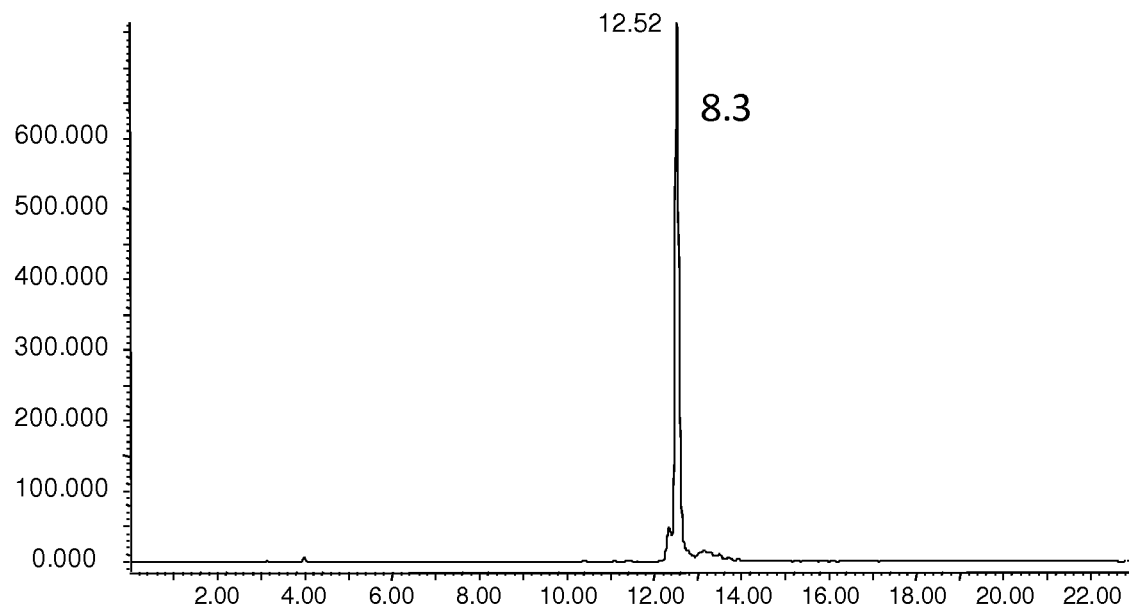
Figure 10:
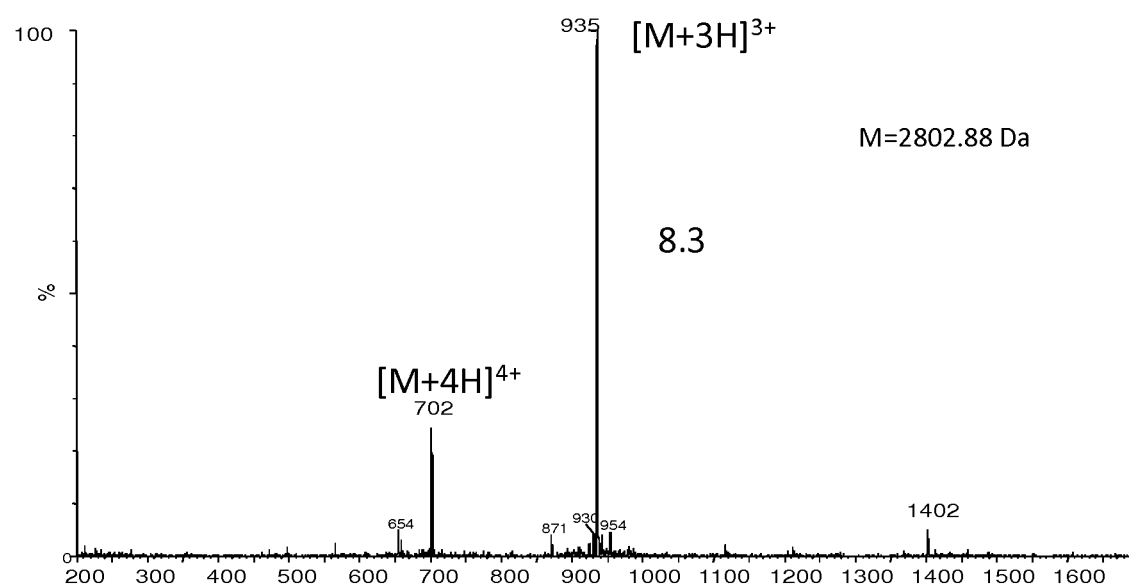

FIG. 3: RP-HPLC chromatogram of peptide 4
FIG. 4: MS spectrum of peptide 4
FIG. 5: RP-HPLC chromatogram of peptide 5.1a
FIG. 6: MS spectrum of peptide 5.1a
FIG. 7: RP-HPLC chromatogram of peptide 8.2
FIG. 8: MS spectrum of peptide 8.2
FIG. 9: RP-HPLC chromatogram of peptide 8.3
FIG. 10: MS spectrum of peptide 8.3
FIG. 11: RP-HPLC chromatogram of peptide 11a
FIG. 12: MS spectrum of peptide 11a
FIG. 13: RP-HPLC chromatogram of the purified peptide 11a
FIG. 14: RP-HPLC chromatogram of peptide 16a
FIG. 15: MS spectrum of peptide 16a
FIG. 16: RP-HPLC chromatogram of peptide 19
FIG. 17: MS spectrum of peptide 19
FIG. 18: RP-HPLC chromatogram of peptide 21
FIG. 19: MS spectrum of peptide 21
FIG. 20: RP-HPLC chromatogram of peptide 23.1
FIG. 21: MS spectrum of peptide 23.1
FIG. 22: RP-HPLC chromatogram of peptide 26.1
FIG. 23: MS spectrum of peptide 26.1
FIG. 24: RP-HPLC chromatogram of peptide 29
FIG. 25: MS spectrum of peptide 29

EXPERIMENTAL SECTION

I—Synthesis of Peptide 11

H-GILKEPVQGA-CHHLEPGG-CHHLEPAG-CILKEPVHGA-NH₂ (SEQ ID NO: 3)

Peptide 11a is prepared by successive ligations of four peptide fragments according to the diagram shown in FIG. 2.

I-A—Preparation of
N₃-Esoc-GILKEPVQGA-SEAoff (peptide 4): (SEQ ID NO: 10)

The N₃-Esoc group is described in document WO2011/058188:

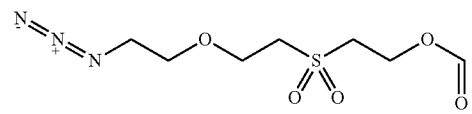

The peptide designated X₁ in FIG. 2 is GILKEPVQGA. (SEQ ID NO: 1)

The preparation of N₃-Esoc-GILKEPVQGA-SEAoff (SEQ ID NO: 10) is illustrated in the following Diagram 3.

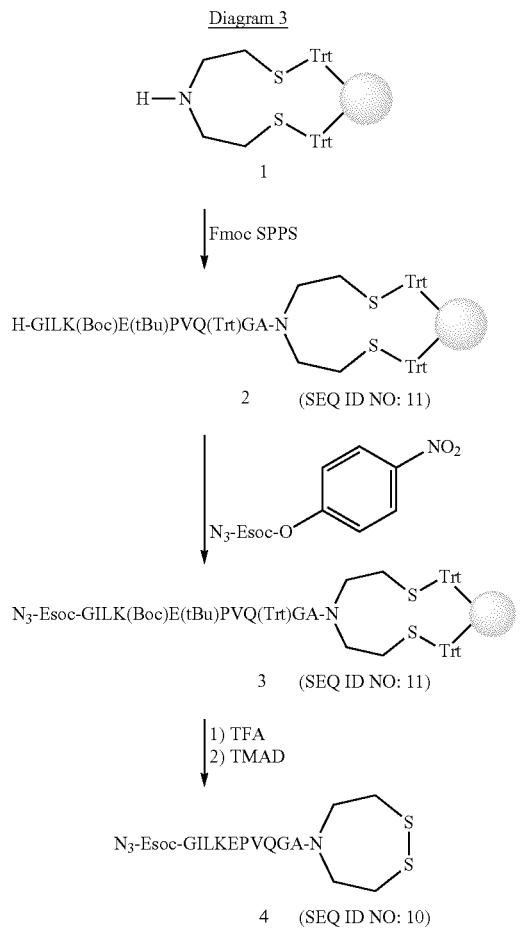

Procedure:
Synthesis of the Peptidyl Resin 2 H-GILK(Boc)E(tBu)PVQ(Trt)GA-SEA-PS (SEQ ID NO: 11)

The solid support SEA-PS (with PS=polystyrene) is described in application FR-2952058.

This peptidyl resin is synthesized at a scale of 0.25 mmol following the protocol described in Ollivier, N.; Dheur, J.; Mhidia, R.; Blanpain, A.; Melnyk, O. Organic Letters 2010, 12, 5238-41.

After synthesis, the resin is washed successively with CH₂Cl₂ (2×2 min) and then with DMF (2×2 min) and is used in the next step.

Synthesis of the Fragment N₃-ESOC-GILKEPVQGA-SEAoff 4: (SEQ ID NO: 10)

The activated arm N3-Esoc-ONp (Diagram 3) is synthesized according to the procedure described in WO2011/058188. This mixed carbonate of 2-[2-(2-azido-ethoxy)-ethylsulphonyl]ethyl and 4-nitrophenyl (145 mg, 0.4 mmol, 1.5 eq) is dissolved in a minimum quantity of DMF and then transferred directly onto the resin. N-Methylmorpholine (55 µL, 0.5 mmol, 2 eq) is added. The reaction mixture is stirred for 12 hours under an argon atmosphere at ambient temperature. The resin is washed successively with DMF (2×2 min), CH₂Cl₂ (2×2 min) and Et2O (2×2 min) and then dried under vacuum.

Final deprotection of the side chains and detachment of the peptide from the resin are carried out by the action of a TFA/TIS/DMSO/H₂O mixture (20 mL, 92.5/2.5/2.5/2.5% v/v) for 1.5 h. The peptide is precipitated from a cold mixture of diethyl ether/heptane (200 mL, 1:1 v/v), centrifuged, and then dissolved in a minimum quantity of water and lyophilized.

The crude peptide 4 (30 mg, 0.02 mmol) is dissolved in sodium phosphate buffer (20 mL, 0.2 M, pH=7.2) and then oxidized in the presence of N,N,N'N'-tetramethylazodicarboxamide (TMAD) (6.8 mg, 0.04 mmol, 2 eq) for 20 minutes. The reaction mixture is purified directly by reversed-phase high-performance liquid chromatography (RP-HPLC) (C18 Nucleosil column (d=1 cm, L=20 cm, 120 Å, 5 µm), UV detection (λ 215 nm), buffer A: H₂O/TFA (1:0.05% v/v), buffer B: CH₃CN/H₂O/TFA (4:1:0.05% v/v/v), gradient: buffer B (0 to 20% in 5 min then 20 to 42% in 60 min, 6 mL/min)). 15 mg of peptide 4 is obtained (Yld=14%). The result of the analysis is shown in FIG. 3.

LC-MS Analysis:
LC-MS: buffer A: H₂O/TFA (1:0.05% v/v), buffer B: CH₃CN/H₂O/TFA (4:1:0.05% v/v/v). RP-HPLC on a C18 Xbridge BEH column (300 Å, 3.5 µm, 4.6×150 mm) using a linear gradient 0-100% B in 30 min, flow rate 1 mL/min, ELS detection.

MS: Positive electrospray ionization mode, cone voltage 30V, quadrupole analyser. Result illustrated in FIG. 4.

I-B—Preparation of the Peptidyl Resin P-1-(1,2,3-triazolyl)-Esoc-GILKEPVQGA-SEAoff (SEQ ID NO: 10), with P=PEGA 800, 5.1

Preparation of P-1-(1,2,3-triazolyl)-Esoc-GILKEPVQGA-SEAoff (SEQ ID NO: 10) is illustrated in Diagram 4 below.

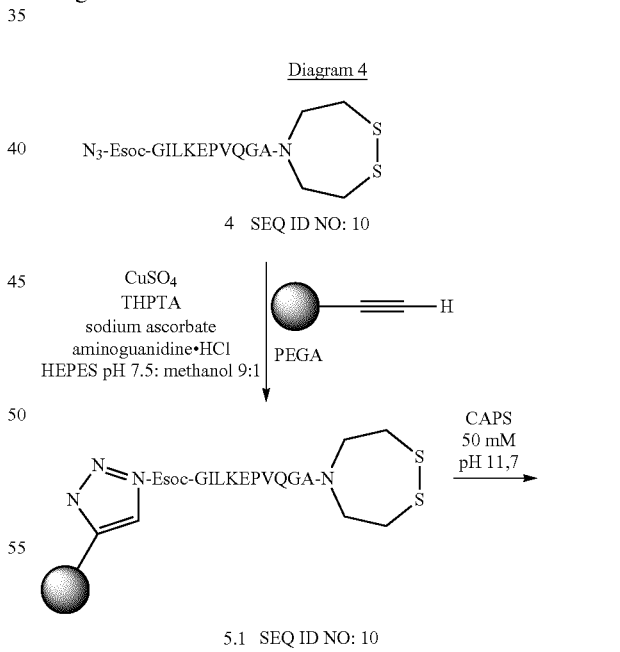

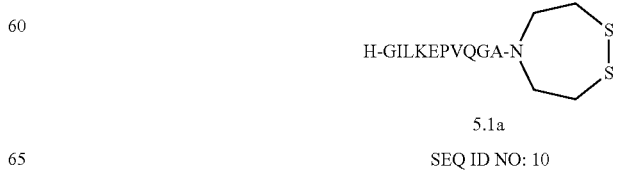

Procedure:

The resin Aminomethyl PEGA 800 (0.4 mmol/g) is coupled with pentynoic acid according to the procedure described in WO2011/058188. The resultant alkyne resin (2 eq) is added to a solution of the azidopeptide 4 (10 µmol) in 1.67 ml of a 9:1 mixture of HEPES 100 mM buffer pH=7.5 and methanol. The resultant suspension is deoxygenated by bubbling continuously with argon (30 min), and then aminoguanidine hydrochloride (1.1 mg, 1 eq), tris(hydroxypropyl)triazolylmethyl-amine (THPTA) (260 mg, 60 eq), copper sulphate pentahydrate (75 mg, 30 eq) and sodium ascorbate (119 mg, 60 eq) are added and the suspension is stirred by bubbling with argon for 30 min at AT. The peptidyl resin 5.1 is then washed successively with copious quantities of: water (deionized), a solution of EDTA 250 mM pH 4.2, water, methanol, DMF and finally water.

Grafting is controlled by treating a small quantity of peptidyl resin with a 50 mM solution of CAPS, the pH of which was adjusted to 11.7 with soda (2×30 min), followed by acidification to pH 32 3 with TFA.

HPLC and MS analysis of 5.1a:

HPLC: buffer A: $H_2O$/TFA (1:0.1% v/v), buffer B: $CH_3CN$/TFA (1:0.1% v/v/v). Result in FIG. 5. RP-HPLC on a C18 Nucleosil column (300 Å, 5 µm, 4.6×250 mm) using a linear gradient 25-45% B in 20 min, flow rate 1 mL/min, DAD detection. Result in FIG. 6.

I-C—Conversion of Resin 5.1 to Thioester Resin 6.1

A solution of tris(2-carboxyethyl)phosphine (TCEP) at 300 mmol/L is prepared in a 0.2 M phosphate buffer at pH=7.3. 3-Mercaptopropionic acid (MPA) (10 vol %, 0.1 mL, 1.14 mmol) is then added. The pH of the solution obtained is adjusted to pH=4.

The preceding solution (V=200 µL) is added to the resin 5.1 (4.5 µmol) packaged in a syringe equipped with a frit. The reaction mixture is stirred for 24 h at T=37° C. The resin is washed (3×300 µL×1 min) with a solution of 3-mercaptophenylacetic acid (MPAA, 500 mmol/L) prepared in 0.1 M sodium phosphate buffer at pH=7.2.

I-D—Ligation of Peptide 7.1
H-C(StBu)HHLEPGG-SEAoff (SEQ ID NO: 12)

Synthesis of the Peptidyl Resin 5.2. Cycle 1

The experiment is carried out in a glove box ($[O_2]$<50 ppm). The peptide 7.1 (9.4 mg, 0.0068 mmol, 1.5 eq) is dissolved in the aforementioned solution of MPAA (270 µL 500 mmol/L, phosphate buffer pH=7.2) and then transferred onto the peptidyl resin 6.1. The reaction mixture is stirred for 24 h at 37° C. After reaction, the resin is drained and then washed with buffer A ($H_2O$/TFA)(1/0.05% v/v, 3×300 µL×2 min).

LC-MS analysis: RP-HPLC chromatogram of 8.2. See FIG. 7: the largest peak 8.2 represents the product 8.2 isolated in the form of dimer (disulphide). This dimer forms during cleavage of the product in basic medium, by oxidation in the air.

LC-MS: buffer A: $H_2O$/TFA (1/0.05% v/v), buffer B: $CH_3CN$/$H_2O$/TFA (4/1/0.05% v/v/v). RP-HPLC on a C18 Xbridge BEH column (300 Å, 3.5 µm, 4.6×150 mm) using a linear gradient 0-100% B in 30 min, flow rate=1 mL/min, ELS detection. MS: Positive electrospray ionization mode, cone voltage 30V, quadrupole analyser. See FIG. 8: the largest peaks represent the product 8.2 isolated in the form of dimer (disulphide).

I-E—Conversion of the Peptidyl Resin 5.2 to resin 6.2

The peptidyl resin 5.2 is converted to resin 6.2 thioester of MPA using the protocol used above for converting 5.1 to 6.1.

I-F—Synthesis of the Peptidyl Resin 5.3. Cycle 2

The peptide 7.2 (X=Ala, 9.5 mg, 0.0068 mmol, 1.5 eq) is reacted with the peptidyl resin 6.2 using a synthesis protocol strictly identical to that used for the peptidyl resin 5.2 (cycle 1).

LC-MS analysis: RP-HPLC chromatogram of 8.3 See FIG. 9.

LC-MS: buffer A: $H_2O$/TFA (1/0.05% v/v), buffer B: $CH_3CN$/$H_2O$/TFA (4/1/0.05% v/v/v). RP-HPLC on a C18 Xbridge BEH column (300 Å, 3.5 µm, 4.6×150 mm) using a linear gradient 0-100% B in 30 min, flow rate 1 mL/min, ELS detection. MS: Positive electrospray ionization mode, cone voltage 30V, quadrupole analyser. See FIG. 10.

I-G—Synthesis of the Peptide
H-CILKEPVHGA-$NH_2$ (peptide 9) (SEQ ID NO: 2)

The synthesis of this peptide is described in:
Ollivier, N.; Dheur, J.; Mhidia, R.; Blanpain, A.; Melnyk, O. Organic Letters 2010, 12, 5238-41.

I-H—Synthesis of Peptide 11a

The reaction is carried out in a glove box ($[O_2]$<50 ppm) under nitrogen atmosphere. A solution of TCEP at 300 mmol/L is prepared in a 0. 2M phosphate buffer at pH =7.3. 3-Mercaptophenylacetic acid (MPAA 84 mg, 0.5 mmol) is then added. The pH of the TCEP/MPAA solution obtained is adjusted to pH=6.5.

Peptide 9 (4.6 mg, 0.0068 mmol, 1.5 eq) is dissolved in the preceding solution of TCEP/MPAA (110 µL) and then transferred onto the peptidyl resin 5.3. The reaction medium is stirred for 24 h at 37° C. After the ligation reaction, the peptidyl resin 10 is drained and then washed with buffer A ($H_2O$/TFA (1/0.05% v/v) (3×300 µL×2 min).

Cleavage of the peptidyl resin 11 is carried out in a glove box ($[O_2]$<50 ppm). The peptidyl resin 11 is cleaved by adding a solution of NaOH (500 µL, $10^{-2}$ M), with stirring for 15 min at 37° C. The beads are filtered, washed and the filtrate is lyophilized.

Peptide 11a is purified directly by reversed-phase high-performance liquid chromatography (RP-HPLC) (C18 Nucleosil column (d=1 cm, L=20 cm, 120 Å, 5 µm), UV detection (215 nm), buffer A: $H_2O$/TFA (1:0.05% v/v), buffer B: $CH_3CN$/$H_2O$/TFA (4:1:0.05% v/v/v), gradient: buffer B (0 to 20% in 5 min then 20 to 42% in 60 min, 6 mL/min)). 4.2 mg of peptide 11 is obtained (Yld=21%).

Figure 11:
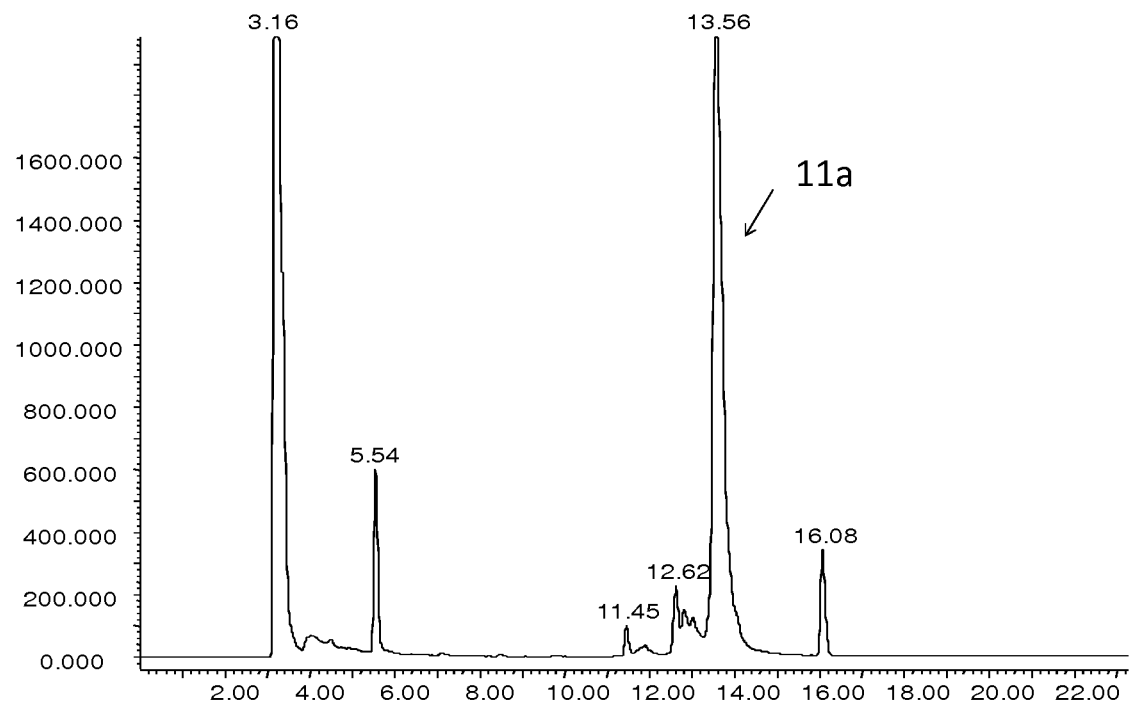

LC-MS analysis. RP-HPLC chromatogram of peptide 11a. The chromatogram is shown in FIG. 11.

Figure 12:
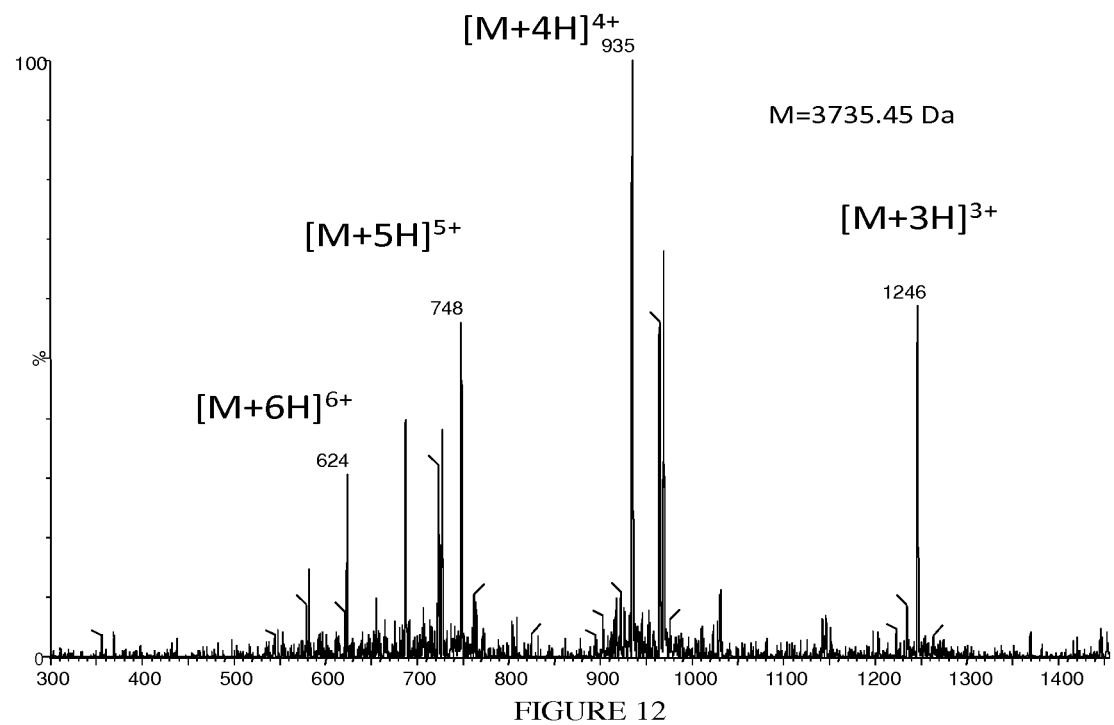

LC-MS: buffer A: $H_2O$/TFA (1/0.05% v/v), buffer B: $CH_3CN$/$H_2O$/TFA (4/1:0.05% v/v/v). RP-HPLC on a C18 Xbridge BEH column (300 Å, 3.5 µm, 4.6×150 mm) using a linear gradient 0-100% B in 30 min, flow rate 1 mL/min, ELS detection. MS: Positive electrospray ionization mode, cone voltage 30V, quadrupole analyser. The mass spectrum is shown in FIG. 12.

Figure 13:
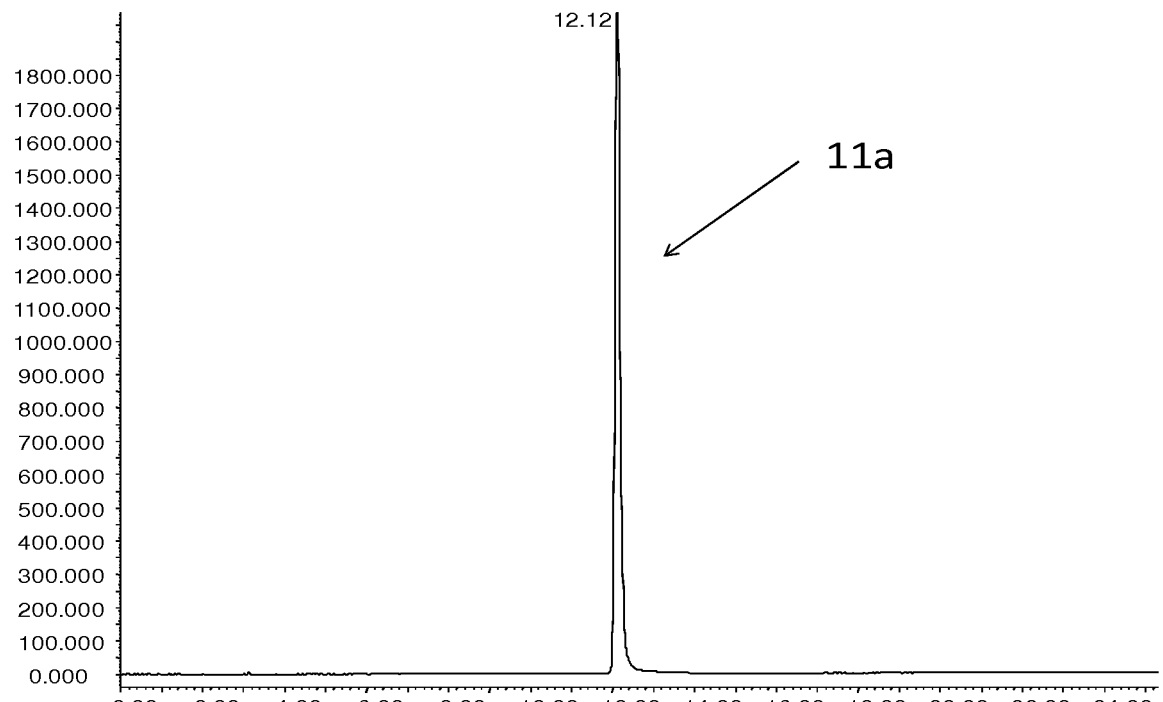

RP-HPLC chromatogram of the purified peptide 11a. The chromatogram is shown in FIG. 13.

II—Synthesis of the Peptide H-CHHLEPGG-CILKEPVHGA-NH$_2$ 16a (SEQ ID NO: 4)

II-A—Synthesis of Resin 12: Pal-ChemMatrix 5-amino-5-oxopentanoic Acid

The following Diagram 5 is followed:

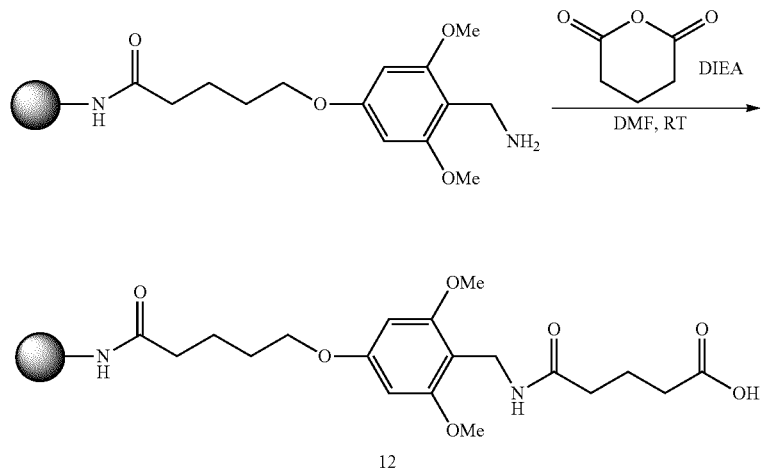

Diagram 5

Procedure: Pentanedioic anhydride (129 mg, 1 mmol, 10 eq) is dissolved in a minimum quantity of DMF and is then transferred directly onto the Pal-ChemMatrix resin (263 mg, 0.1 mmol, δ=0.43 mmol/g, 1 eq). N,N-Diisopropylethylamine (DIEA) (197 µL, 1 mmol, 10 eq) is added. The reaction medium is stirred for 1.5 hours under argon atmosphere at ambient temperature. The resin is washed successively with DMF (2×2 min), CH$_2$Cl$_2$ (2×2 min), and then drained. A TNBS test is carried out to verify the absence of free amine.

II-B—Synthesis of Resin 13: PAL-ChemMatrix N-(3-amino-2-hydroxypropyl)amide

This synthesis is carried out according to the following Diagram 6:

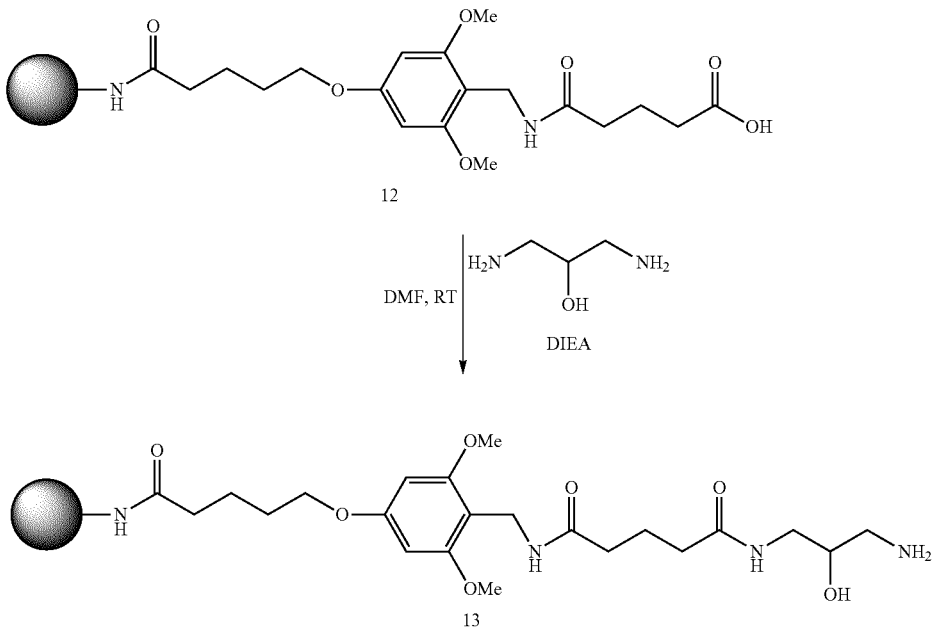

Diagram 6

Procedure: 1,3-Diamino-2-propanol (99 mg, 1 mmol, 10 eq) and benzotriazol-1-yloxy-tripyrrolidinophosphonium hexafluorophosphate (PyBOP) (114 mg, 0.2 mmol, 2 eq) are dissolved in a minimum quantity of DMF and then transferred directly onto the resin 12. DIEA (191 µL, 1 mmol, 10 eq) is added. The reaction mixture is stirred for 2 hours under argon atmosphere at ambient temperature. Resin 13 is washed successively with DMF (2×2 min), CH$_2$Cl$_2$ (2×2 min), and then drained. A TNBS test is carried out to verify presence of free amine.

II-C—Synthesis of the Thiazolidine Peptidyl Resin 15

This synthesis is carried out according to the following Diagram 7:

Procedure: The oxidizing agent sodium periodate (NaIO$_4$) (1.2 mg, 5.7 µmol, 4 eq) is dissolved in a minimum quantity of 0.1 M phosphate buffer at pH=7.2 and then transferred onto resin 13 (7.2 mg, 2.9 µmol, 2 eq). The reaction medium is stirred for 15 minutes at ambient temperature. The excess of oxidizing agent is then neutralized by the addition of ethanolamine (1.4 µL, 22.9 µmol, 16 eq) to the resin. After stirring, the resin 14 is washed with 0.1 M phosphate buffer at pH=6.

Handling is carried out in a glove box ([O$_2$]<50 ppm). The peptide 7.1 (2 mg, 1.4 µmol, 1 eq) is dissolved in V=72 µL of a solution of MPAA 500 mmol/L prepared in 0.1 M phosphate buffer at pH=6. The solution of peptide is transferred onto the aforementioned resin 14. The reaction mixture is stirred for 24 hours at 37° C. The excess aldehyde is neutralized with V=200 µL of a solution of methylhydroxylamine (14 mmol/L prepared in ammonium acetate buffer at pH=4.5). After stir-

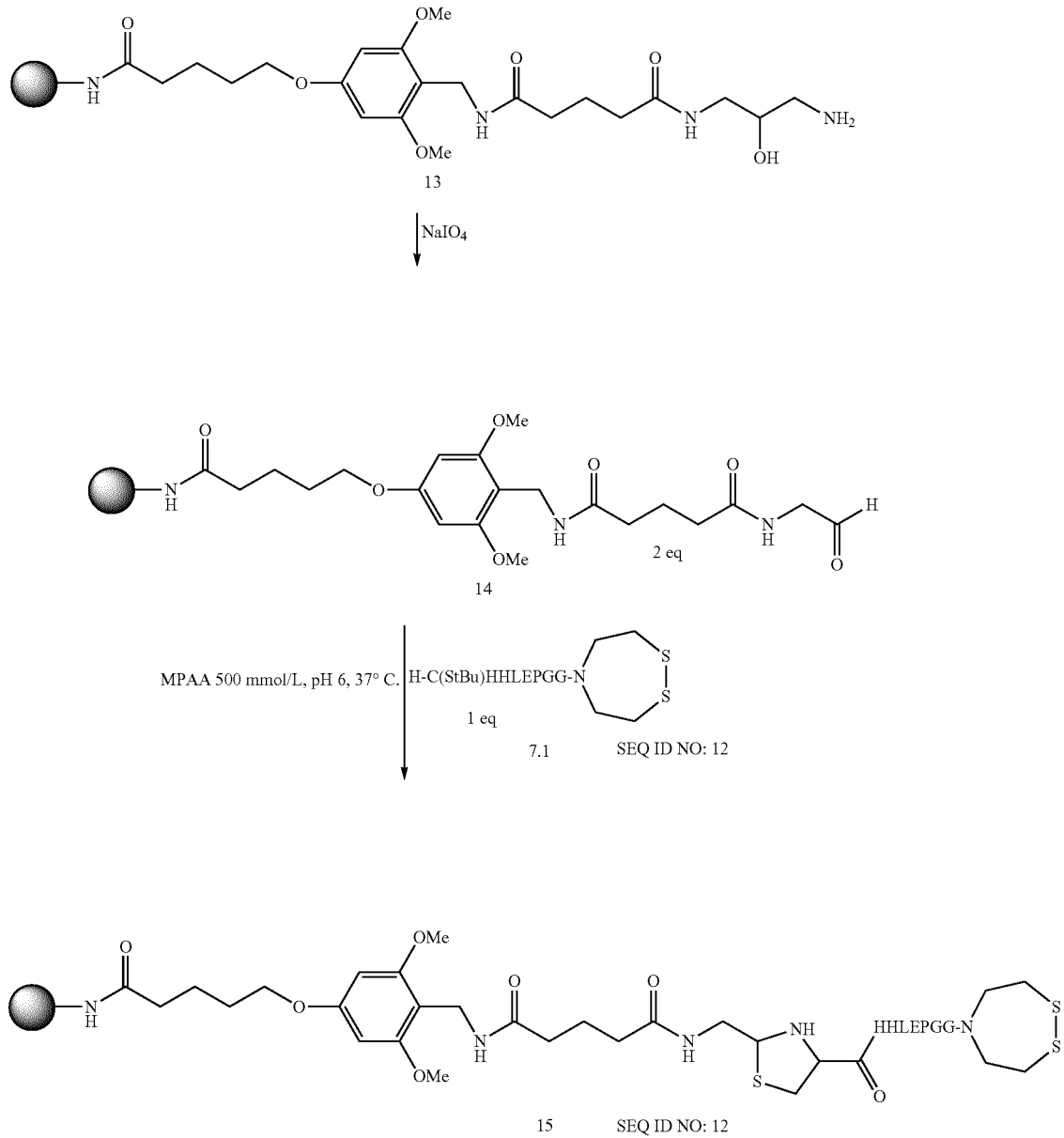

Diagram 7 ring, resin 15 is drained and then washed (3*300 mL×2 min) with phosphate buffer at pH=7.2.

II-D—Ligation of Peptide 9 H-CILKEPVHGA-NH₂ (SEQ ID NO: 2)

Synthesis of the Peptidyl Resin 16:
This synthesis is carried out according to the following Diagram 8:

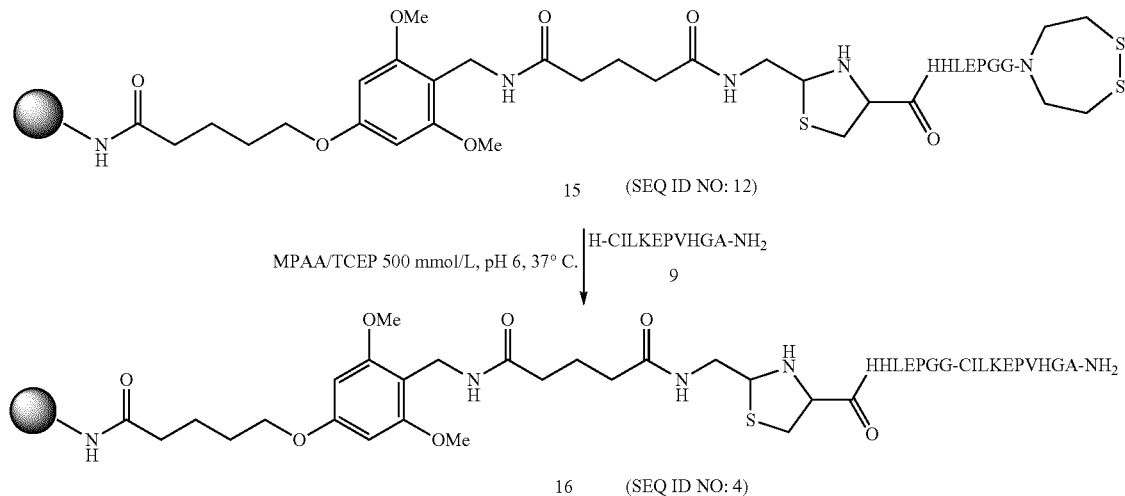

Procedure: Handling is carried out in a glove box ([O₂]<50 ppm). A solution of TCEP at 300 mmol/L is prepared in 0.2 M phosphate buffer at pH=7.2. 3-Mercaptophenylacetic acid (MPAA) (84 mg, 0.5 mmol) is then added. The pH of the TCEP/MPAA solution obtained is adjusted to pH=6.5.

Peptide 9 (3 mg, 2.1 μmol, 1.5 eq) is dissolved in V=70 μL of the preceding solution of TCEP/MPAA and then transferred onto the peptidyl resin 15. The reaction medium is stirred for 24 h at T=37° C. After the ligation reaction, resin 16 is drained and then washed with buffer A: H₂O/TFA (1:0.05% v/v) (3×300 μL×2 min).

II-E—Cleavage of the Peptidyl Resin 16, Synthesis of Peptide H-CHHLEPGG-CILKEPVHGA-NH₂ 16a (SEQ ID NO: 4)

This synthesis is carried out according to the following diagram:

Procedure: Handling is carried out in a glove box ([O₂]<50 ppm). The peptidyl resin 16 is cleaved by adding V=500 μL of a solution of methylhydroxylamine (300 mmol/L at pH=3 prepared in phosphate buffer) with stirring for 3 hours at 37° C. The beads are filtered, washed and the filtrate is lyophilized.

LC-MS analysis RP-HPLC chromatogram of peptide 16a H-CHHLEPGG-CILKEPVHGA-NH₂ (SEQ ID NO: 4)

Figure 14:
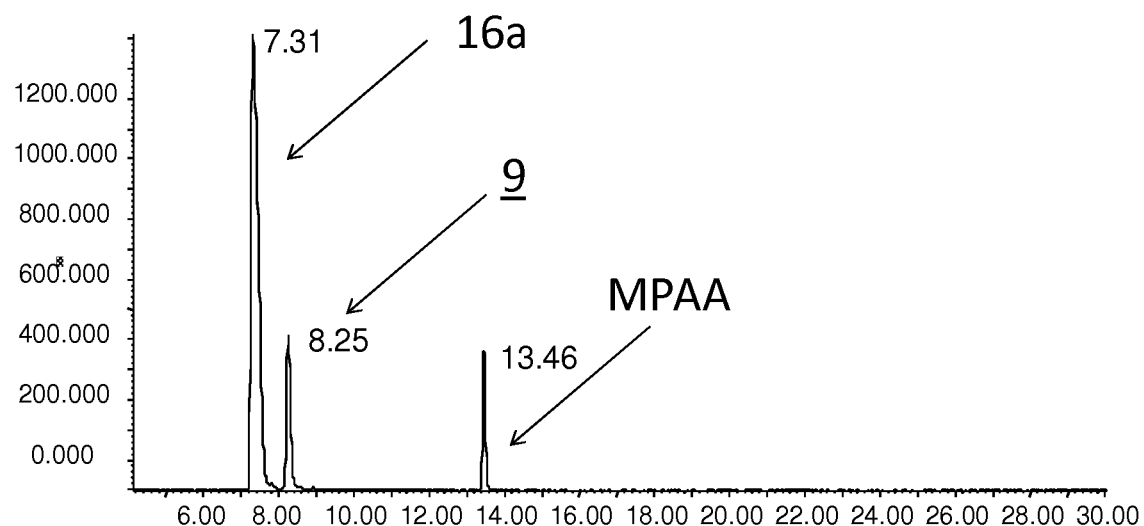
Figure 15:
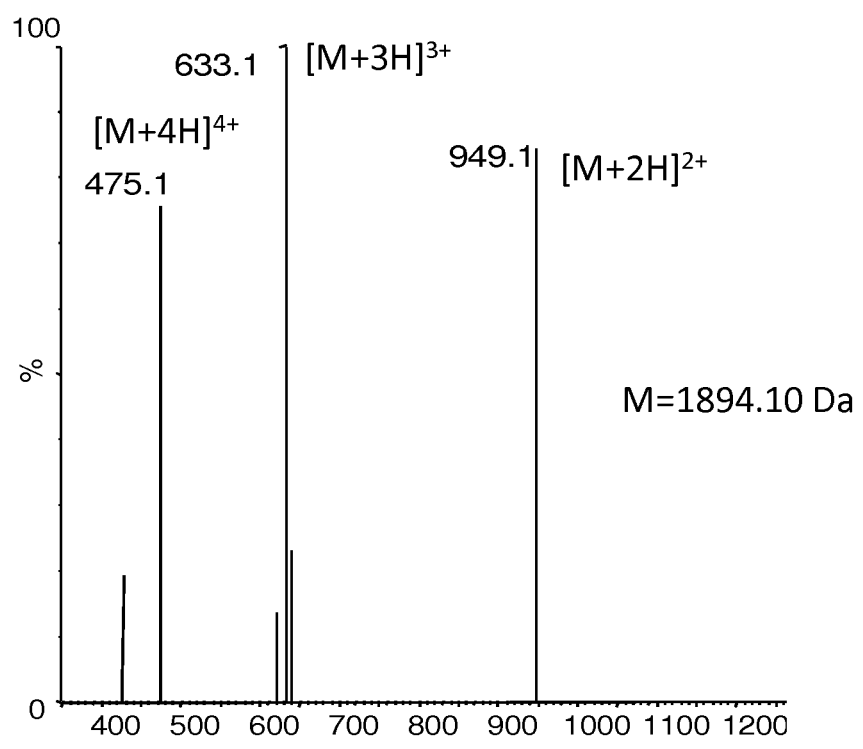

LC-MS: buffer A: H₂O/TFA (1:0.05% v/v), buffer B: CH₃CN/H₂O/TFA (4:1:0.05% v/v/v). RP-HPLC on a C18 Xbridge BEH column (300 Å, 3.5 μm, 4.6×150 mm) using a linear gradient A/B: 0-100% B in 30 min, flow rate=1 mL/min, ELS detection. MS: Positive electrospray ionization mode, cone voltage 30V, quadrupole analyser. FIG. 14 illustrates the RP-HPLC spectra obtained: the peak marked RsMPAA represents the residues of MPAA. The mass spectrum is shown in FIG. 15.

Synthesis of the Peptide H-AAAAAKDYIRN-CI-IGKGRSYKGTVSITKSGIK-CQPWSSMIPHEHS-FLPSSYRGKDLQENY-CRNPRGEEGGPWCFTSNPE-VRYEVCDIPQCSEVK(biotin)-NH₂ 29 (SEQ ID NO: 5)

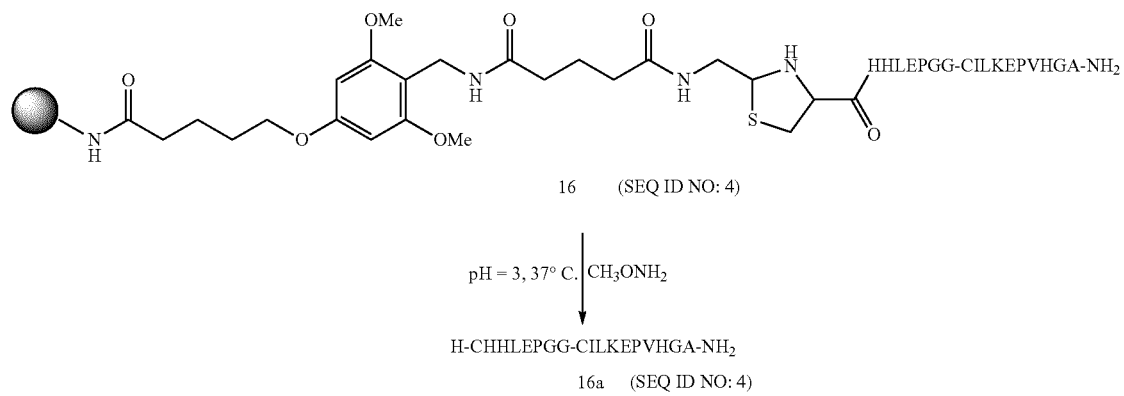

III-A—Synthesis of the Fragment N₃-ESOC-AAAAAKDYIRN-SEAoff 19 (SEQ ID NO: 6)

This synthesis is carried out according to the following diagram:

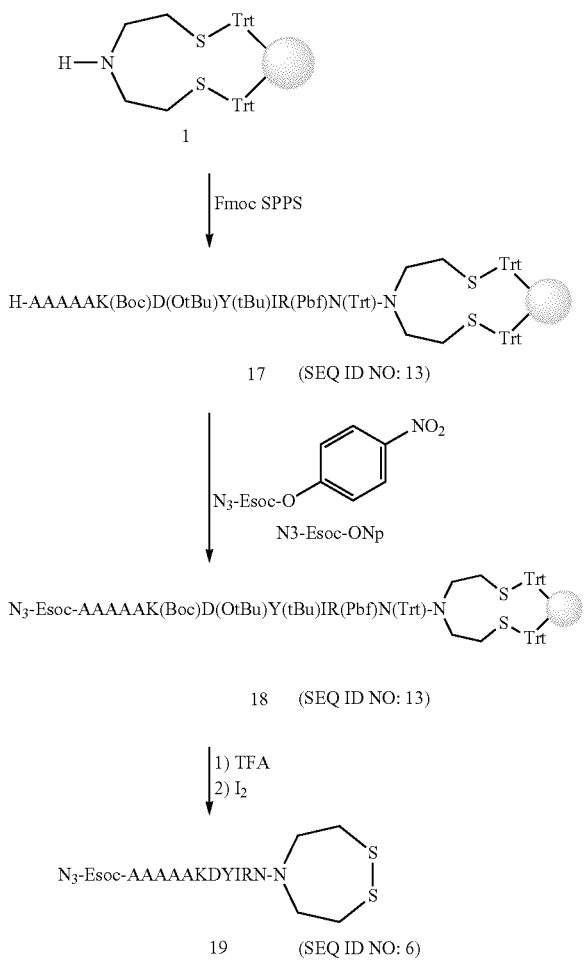

Synthesis of the Peptidyl Resin 17 H-AAAAAK(Boc)D(OtBu)Y(tBu)IR(Pbf)N(Trt)-SEA-PS (PS=Polystyrene) (SEQ ID NO: 13)

This peptidyl resin is synthesized at a scale of 0.25 mmol following the protocol described in Ollivier, N.; Dheur, J.; Mhidia, R.; Blanpain, A.; Melnyk, O. Organic letters 2010, 12, 5238-41.

After synthesis, the resin is washed successively with CH₂Cl₂ (2×2 min) and then DMF (2×2 min), and is used in the next step.

Synthesis of the Fragment N₃-ESOC-AAAAAKDYIRN-SEAoff 19 (SEQ ID NO: 6)

The activated arm N₃-Esoc-ONp is synthesized according to the procedure described in WO2011/058188. This mixed carbonate of 2-[2-(2-azido-ethoxy)-ethylsulphonyl]ethyl and 4-nitrophenyl (145 mg, 0.4 mmol, 1.5 eq) is dissolved in a minimum quantity of DMF and then transferred directly onto the resin 17. N-Methylmorpholine (55 μpL, 0.5 mmol, 2 eq) is added. The reaction mixture is stirred for 12 hours under argon atmosphere at ambient temperature. Resin 18 is washed successively with DMF (2×2 min), CH₂Cl₂ (2×2 min) and Et₂O (2×2 min) and then dried under vacuum.

Final deprotection of the side chains and detachment of the peptide from the resin are carried out by the action of a TFA/TIS/DMSO/H₂O mixture (20 mL, 92.5/2.5/2.5/2.5% v/v) for 1.5 h. The peptide is precipitated from a cold mixture of diethyl ether/heptane (200 mL, 1:1 v/v), centrifuged, and then dissolved in a minimum quantity of water and lyophilized.

The crude peptide 19 (100 mg, 0.05 mmol) is dissolved in sodium phosphate buffer (26 mL, 0.2 M, pH=7.2) and then oxidized in the presence of N,N,N',N'-tetramethylazodicarboxamide (TMAD) (18.4 mg, 0.1 mmol, 2 eq) for 20 minutes. The reaction mixture is purified directly by reversed-phase high-performance liquid chromatography (RP-HPLC) (C18 Nucleosil column (d=1 cm, L=20 cm, 120 Å, 5 μm), UV detection (λ=215 nm), buffer A: H₂O/TFA (1:0.05% v/v), buffer B: CH₃CN/H₂O/TFA (4:1:0.05% v/v/v), gradient: buffer B (0 to 20% in 5 min then 20 to 42% in 60 min, 6 mL/min)). 23 mg of peptide 19 is obtained (Yld=23%).

LC-MS analysis: RP-HPLC chromatogram of 19

LC-MS: buffer A: H₂O/TFA (1/0.05% v/v), buffer B: CH₃CN/H₂O/TFA (4/1/0.05% v/v/v). RP-HPLC on a C18 Xbridge BEH column (300 Å, 3.5 μm, 4.6×150 mm) using a linear gradient 0-100% B in 30 min, flow rate 1 mL/min, ELS detection. MS: Positive electrospray ionization mode, cone voltage 30V, quadrupole analyser.

Figure 16:
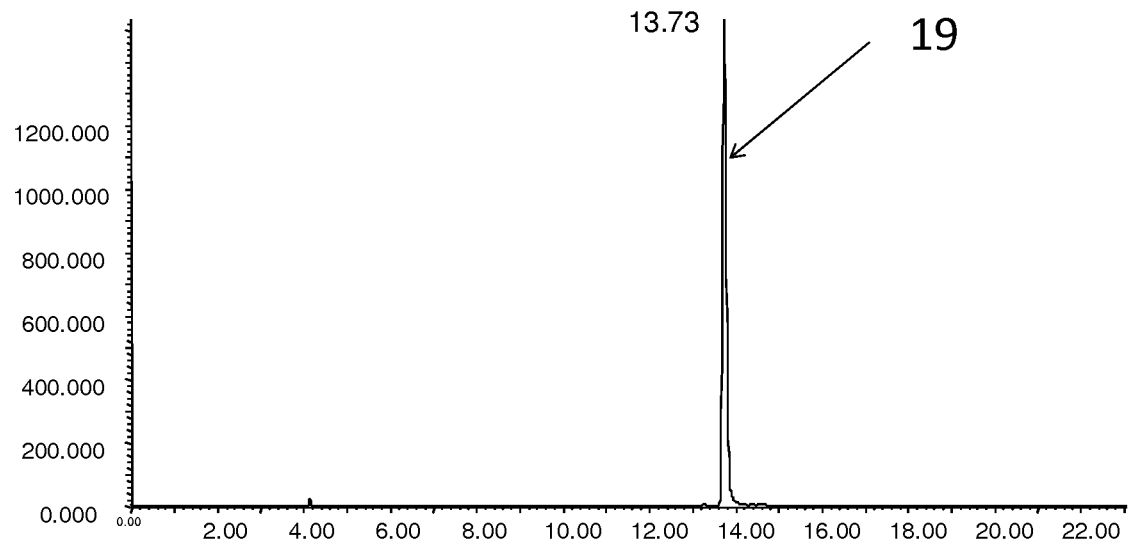
Figure 17:
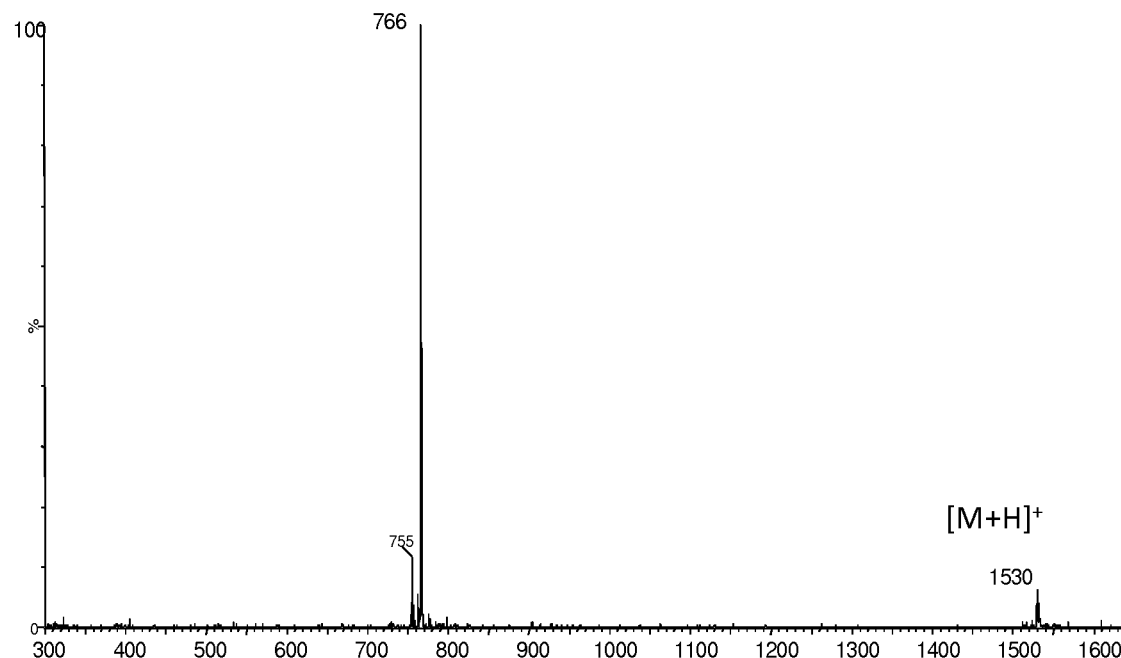

FIG. 16 illustrates the RP-HPLC spectra obtained. The mass spectrum is shown in FIG. 17.

III-B—Synthesis of Peptide 29

This synthesis is carried out according to the following diagram:

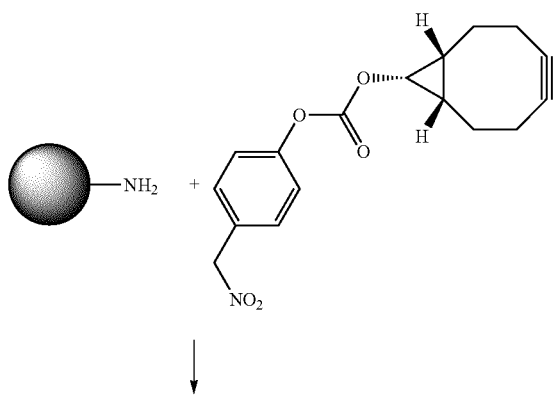

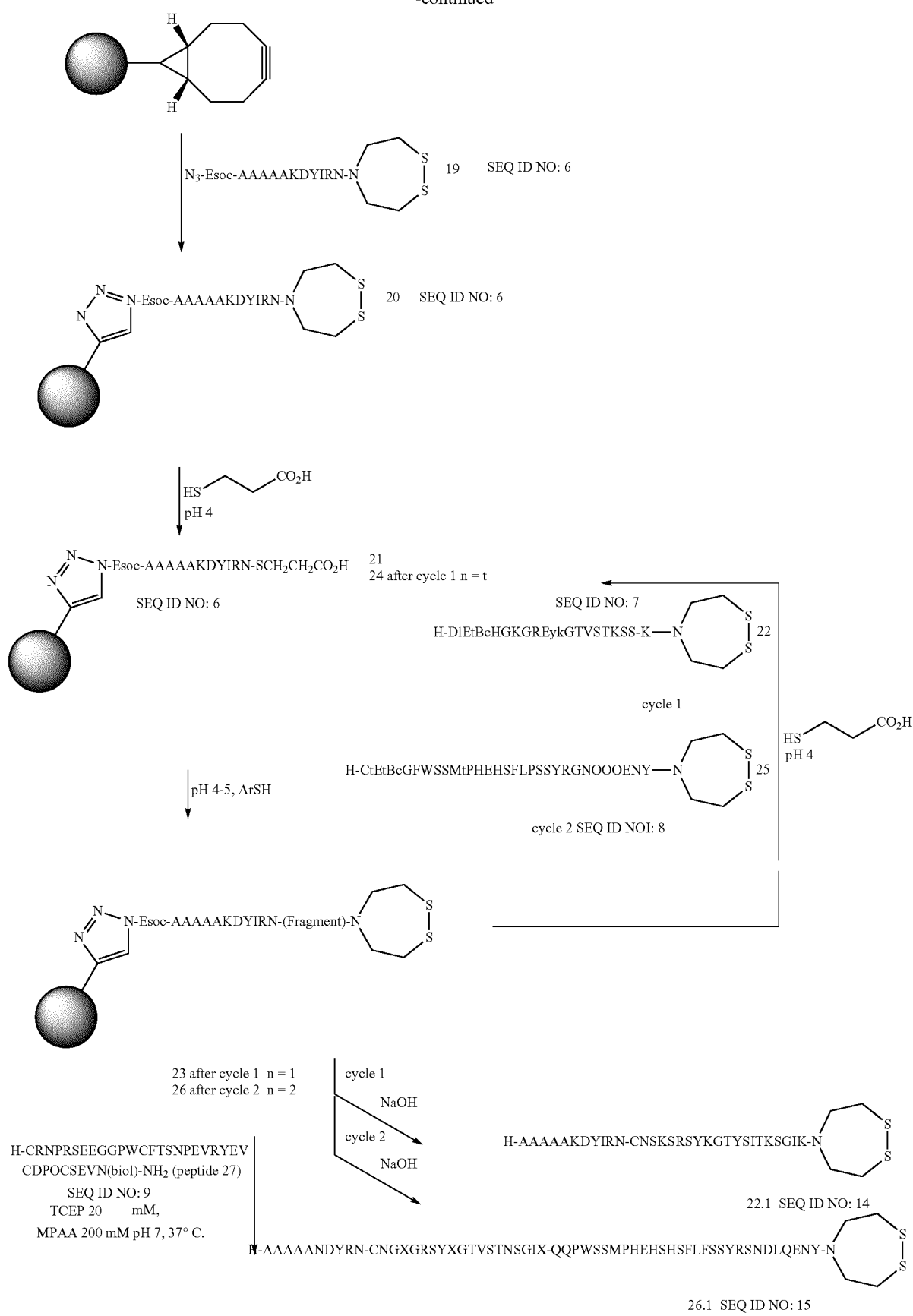

N-Esoc-AAAAAKDYIRN-CHGKGRSYXGTVSITXEGG-CQPWSSMPHEHSFLPSSYRGNDLGENY-
CRNFRGEEGGPWCFTSNPEVRYENCDPQCSEYN-NH$_2$
SEQ ID NO: 5

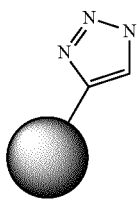

28

↓ NaOH

H-AAAAAKDYIRN-CNGXGRSTKGTVSITXSGN-CQPWEEMIPHEHHEPLPSSYRGKDLQENY-CRNPRSEESSFWCFTBNFEVRYEVCD
PQCSEVN(biol)-NH$_2$
25   SEQ ID NO: 5

Grafting of peptide 19 on a cyclooctyne solid support. Preparation of support 20: The mixed carbonate of bicyclo [6.1.0]non-4-yn-9-ylmethyl and 4-nitrophenyl (176 mg, 0.56 μmol, 3 eq), prepared according to the procedure described in Dommerholt, J. et al., Angewandte Chem., Int. Ed. 2010, 49, 9422-9425, is dissolved in a minimum quantity of DMF and then transferred directly onto the aminomethyl PEGA$^{1900}$ resin (0.4 mmol/g). N,N-Diisopropylethylamine (370 μL, 3.36 mmol, 6 eq) is added. The reaction medium is stirred for 16 hours under an argon atmosphere at ambient temperature. The resin is washed successively with DMF (2×2 min), CH$_2$Cl$_2$ (2×2 min), 20% of piperidine in DMF then MeOH/DMF/AcOH mixture (9:9:2) (5×2 min), and MeOH (2×2 min).

The resultant alkyne resin (2 eq) is added to a solution of the azidopeptide 19 (8.2 μmol) in 2.4 ml of 8:2 mixture of water (deionized) and acetonitrile with 0.1% of TFA. The suspension is stirred at ambient temperature for 80 hours. The peptidyl resin 20 is then washed successively with copious quantities of: acetonitrile with 0.1% of TFA, water with 0.1% of TFA, water, MeOH, DMF, MeOH, and finally water.

Characterization of the peptidyl resin 20. Detachment of the peptide and formation of peptide 21 in solution (H-AAAAAKDYIRN-SEAoff 21) (SEQ ID NO: 6)

20% of piperidine in DMF, MeOH/DMF/AcOH (9:9:2), DMF, MeOH, and finally water.

HPLC analysis: RP-HPLC chromatogram of 21

Buffer A: H$_2$O/TFA (1:0.1% v/v), buffer B: CH$_3$CN/TFA (1:0.1% v/v/v). RP-HPLC on a C18 Nucleosil column (300 Å, 5 μm, 4.6×250 mm)

using a linear gradient 25-45% B in 20 min, flow rate 1 mL/min,

DAD detection.

Figure 18:
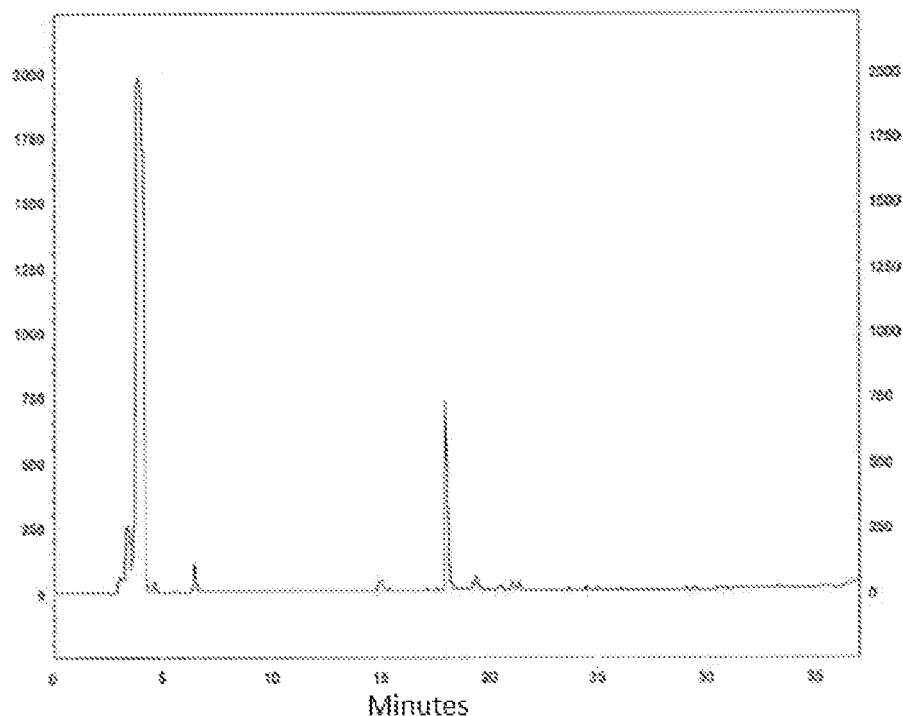
Figure 19:
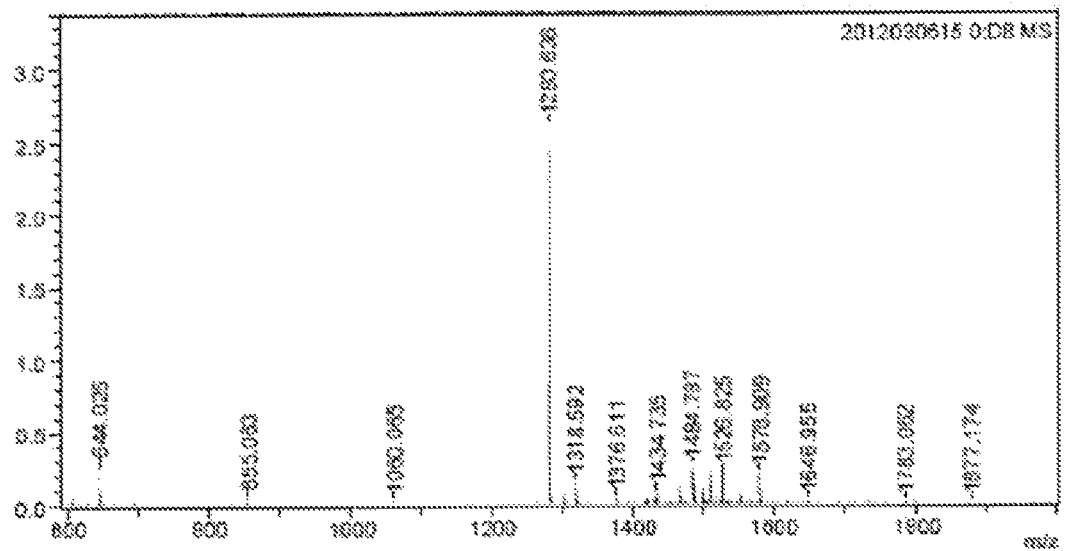

FIG. 18 illustrates the RP-HPLC spectra obtained. The mass spectrum of product 21 is shown in FIG. 19.

Synthesis of Peptide 22 H-C(StBu)IIGKGRSYKGTVSITKSGIK-SEAoff (SEQ ID NO: 7)

This peptide is synthesized at a scale of 0.25 mmol following the protocol described in Ollivier, N.; Dheur, J.; Mhidia, R.; Blanpain, A.; Melnyk, O. *Organic letters* 2010, 12, 5238-41.

Synthesis of Peptide 25 H-C(StBu)QPWSSMIPHEHS-FLPSSYRGKDLQENY-SEAoff (SEQ ID NO: 8)

This peptide is synthesized at a scale of 0.25 mmol following the protocol described in Ollivier, N.; Dheur, J.; Mhidia, R.; Blanpain, A.; Melnyk, O. *Organic letters* 2010, 12, 5238-41.

Synthesis of Peptide 27 H-CRNPRGEEGGPWCFTSN-PEVRYEVCDIPQCSEVK(biotin)-NH$_2$ (SEQ ID NO: 9)

This peptide is synthesized at a scale of 0.25 mmol following the protocol described in Ollivier, N.; Dheur, J.; Mhidia, R.; Blanpain, A.; Melnyk, O. *Organic letters* 2010, 12, 5238-41.

Conversion of Resin 20 to Thioester Resin 21

A solution of tris(2-carboxyethyl)phosphine (TCEP) at 200 mmol/L is prepared in a 0.2 M phosphate buffer in the presence of guanidine (6 M) at pH=7.2. 3-Mercaptopropionic acid (MPA) (5 vol %, 0.05 mL, 0.58 mmol) is then added. The pH of the solution obtained is adjusted to pH=4.

The preceding solution (V=150 μL) is added to resin 20 (0.5 μmol) packaged in a syringe equipped with a frit. The reaction mixture is stirred for 24 h at T=37° C. The resin is washed (3×150 μL×1 min) with a solution of 3-mercaptophenylacetic acid (MPAA, 300 mmol/L) prepared in 0.1 M sodium phosphate buffer in the presence of guanidine (6 M) at pH=7.2.

Ligation of peptide 22 H-C(StBu) IIGKGRSYKGTVSITKSGIK-SEAoff (SEQ ID NO: 7).

Synthesis of the Peptidyl Resin 23

The experiment is carried out in a glove box ([O$_2$]<50 ppm). Peptide 22 (2.3 mg, 0.75 μmol, 1.5 eq) is dissolved in the preceding solution of MPAA (150 μL, 300 mmol/L, 0.1 M phosphate buffer in the presence of guanidine (6 M) at pH 7.2) and then transferred onto the peptidyl resin 21. The reaction medium is stirred for 24 h at 37° C. After reaction, the resin is drained and then washed with 0.2 M sodium phosphate buffer in the presence of guanidine (6 M) at pH=7.2 (3×150 μL×2 min).

Figure 20:
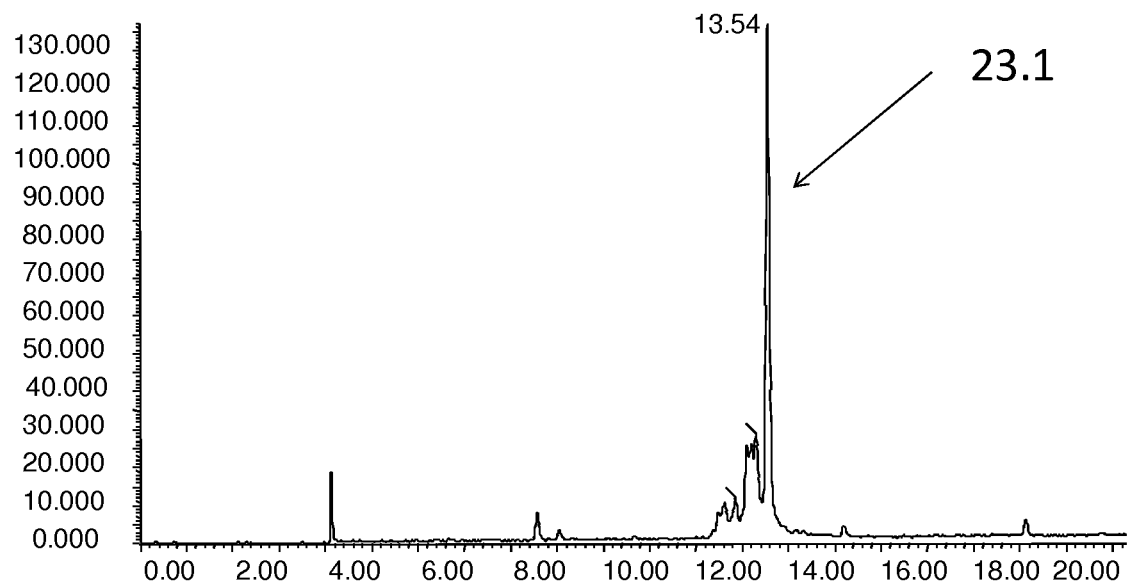

LC-MS analysis: RP-HPLC chromatogram of 23.1 obtained after detachment of the peptide in basic medium starting from the peptidyl resin 23 (FIG. 20).

Figure 21:
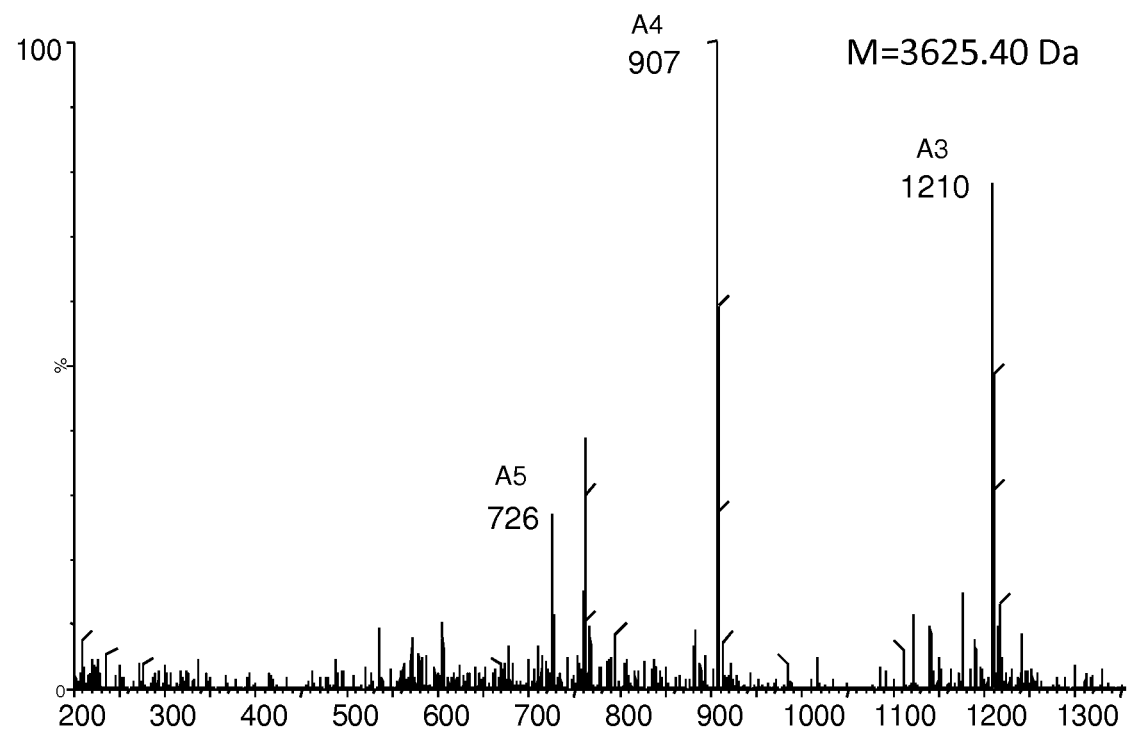

LC-MS: buffer A: H$_2$O/TFA (1/0.05% v/v), buffer B: CH$_3$CN/H$_2$O/TFA (4/1/0.05% v/v/v). RP-HPLC on a C18 Xbridge BEH column (300 Å, 3.5 μm, 4.6×150 mm) using a linear gradient 0-100% B in 30 min, flow rate=1 mL/min, ELS detection. MS: Positive electrospray ionization mode, cone voltage 30V, quadrupole analyser (FIG. 21).

The peptidyl resin 23 is converted to thioester resin 24 of MPA using the protocol used above for converting 20 to 21.

Ligation of peptide 25 H-C(StBu)QPWSSMIPHEHS-FLPSSYRGKDLQENY-SEAoff (SEQ ID NO: 8).

Synthesis of the Peptidyl Resin 26

Peptide 25 (3 *mg, 0.75 μmol, 1.5* eq) is reacted with the peptidyl resin 24 using a synthesis protocol strictly identical to that used for synthesis of peptidyl resin 23 (cycle 1).

Figure 22:
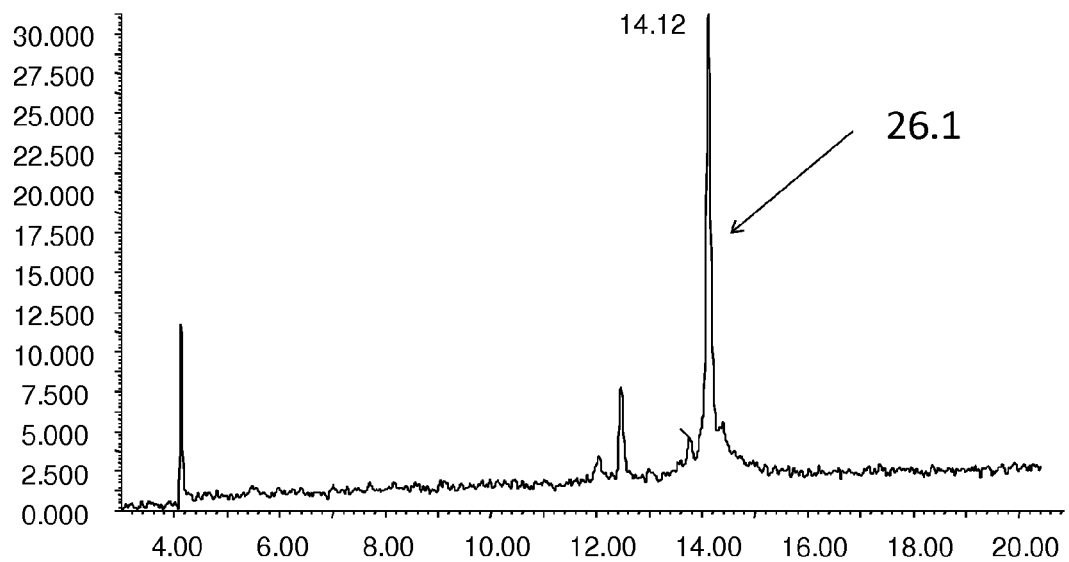

LC-MS analysis: RP-HPLC chromatogram of peptide 26.1 obtained after detachment of the peptide in basic medium starting from peptidyl resin 26 (FIG. 22).

Figure 23:
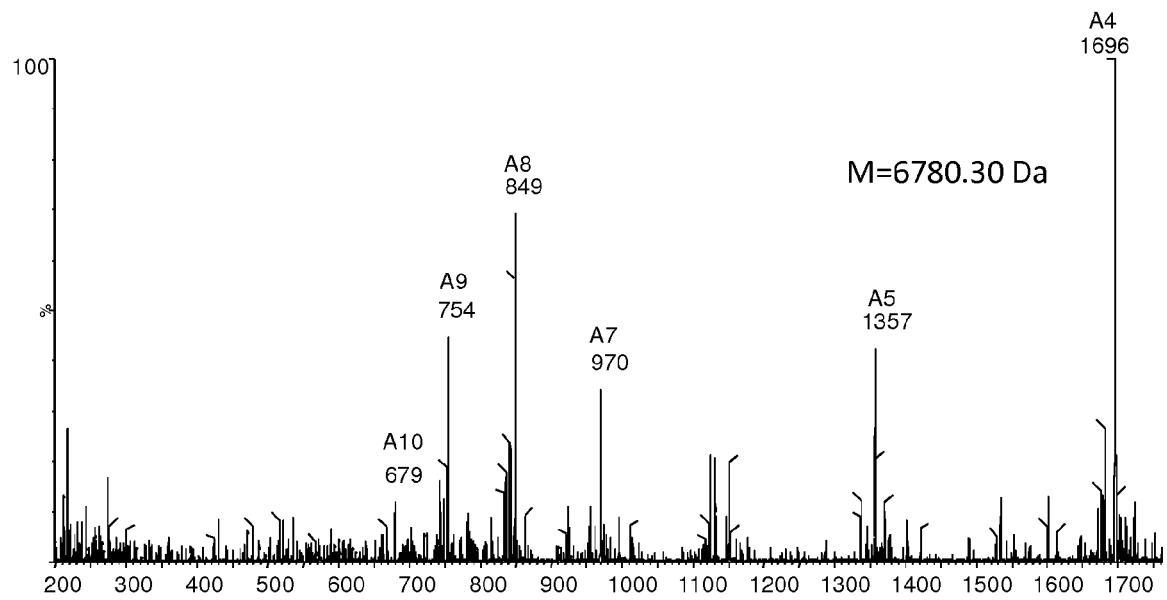

LC-MS: buffer A: $H_2O$/TFA (1/0.05% v/v), buffer B: $CH_3CN$/$H_2O$/TFA (4/1/0.05% v/v/v). RP-HPLC on a C18 Xbridge BEH column (300 Å, 3.5 µm, 4.6×150 mm) using a linear gradient 0-100% B in 30 min, flow rate 1 mL/min, ELS detection. MS: Positive electrospray ionization mode, cone voltage 30V, quadrupole analyser (FIG. 23).

Synthesis of Peptide 29

The reaction is carried out in a glove box ($[O_2]$<50 ppm) under a nitrogen atmosphere. A solution of TCEP at 200 mmol/L is prepared in 0.2 M phosphate buffer in the presence of guanidine (6 M) at pH=7.2. 3-Mercaptophenylacetic acid (MPAA 33 mg, 0.2 mmol) is then added. The pH of the TCEP/MPAA solution obtained is adjusted to pH=6.5.

Peptide 27 (3.4 mg, 0.75 µmol, 1.5 eq) is dissolved in the preceding solution of TCEP/MPAA (150 µL) and then transferred onto the peptidyl resin 26. The reaction medium is stirred for 24 h at 37° C. After the ligation reaction, the peptidyl resin 28 is drained and then washed with 0.2 M sodium phosphate buffer in the presence of guanidine (6 M) pH=7.2.

Cleavage of the Peptidyl Resin 28, Synthesis of Peptide 29

Handling is carried out in a glove box ($[O_2]$<50 ppm). The peptidyl resin 28 is cleaved by adding a solution of NaOH (500 µL, $10^{-2}$ M), with stirring for 5 min at 37° C. The beads are filtered, washed and the filtrate is lyophilized.

LC-MS Analysis

Figure 24:
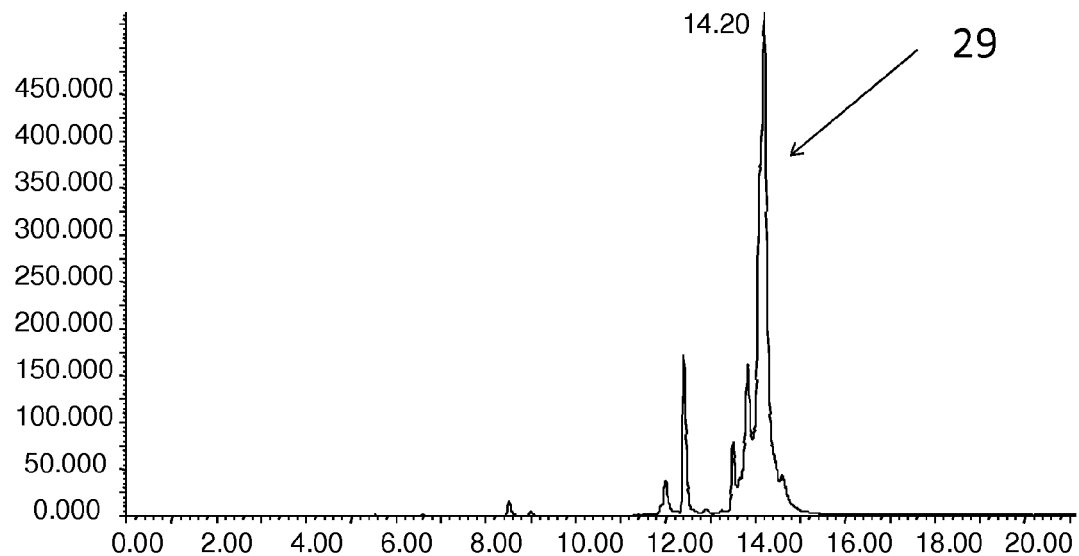

RP-HPLC chromatogram of peptide 29 (FIG. 24)

Figure 25:
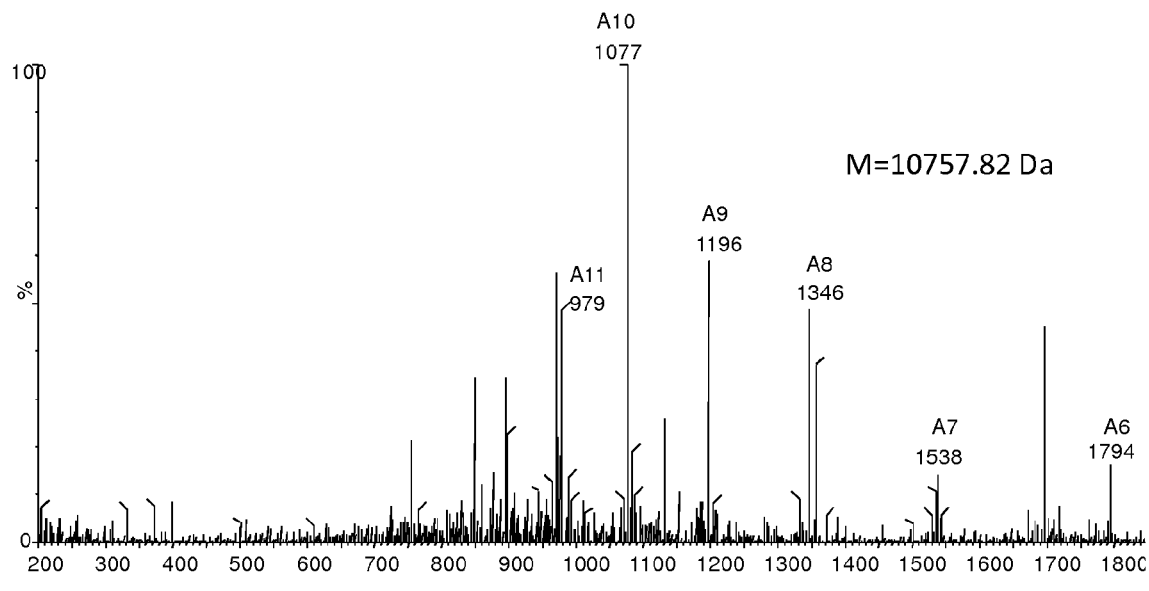

LC-MS: buffer A: $H_2O$/TFA (1/0.05% v/v), buffer B: $CH_3CN$/$H_2O$/TFA (4/1:0.05% v/v/v). RP-HPLC on a C18 Xbridge BEH column (300 Å, 3.5 µm, 4.6×150 mm) using a linear gradient 0-100% B in 30 min, flow rate 1 mL/min, ELS detection. MS: Positive electrospray ionization mode, cone voltage 30V, quadrupole analyser (FIG. 25).

Of course, the present invention is not limited to the examples and to the embodiment described and represented, but is amenable to numerous variants that are within the skills of a person skilled in the art.

The invention claimed is:

1. Method of assembling peptide fragments for manufacturing a polypeptide comprising n peptide fragments and at least n−1 amino acids bearing a thiol function, represented by the formula:

$$A_1\text{-}C_1\text{-}A_2\text{-}C_2\text{-}A_3\text{-} \ldots \text{-}C_{i-1}\text{-}A_i\text{-} \ldots \text{-}C_{n-1}\text{-}A_n \qquad (I)$$

in which $A_1, A_2, A_3, \ldots A_i \ldots, A_n$ are peptide fragments, $C_1, C_2, C_3 \ldots C_{i-1} \ldots C_{n-1}$ are amino acid residues bearing a thiol function, n is comprised between 3 and 50, and i is any integer between 2 and n, said method involving:

(a1) at least one step of preparing a fragment Y-$A_1$-SEAoff ($II_1$) in which $A_1$ represents a peptide fragment the C-terminal of which bears a cyclic bis(2-sulphanylethyl) amino group

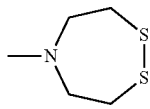

called SEAoff, and

Y is a fragment capable of reacting with a function of a solid support so as to form a bond between $A_1$ and a solid support, (b) at least one step of reaction of Y-$A_1$-SEAoff ($II_1$) with a solid support designated □-Y′, □ representing the solid support itself and Y′ representing a reactive function capable of reacting with Y to form a group Z according to the diagram:

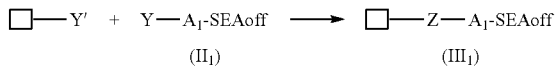

(a2) at least one step of preparing a fragment H-$C_1$(PG$_1$)-$A_2$-SEAoff ($II_2$) in which $C_1$, $A_2$ and SEAoff are as defined above and (PG$_1$) represents H or a protective group of the thiol of the amino acid $C_1$, (c1) at least one step of preparing a thioester peptide of formula ($III_1'$) starting from bis(2-sulphanylethyl)amino peptide □-Z-$A_1$-SEAoff ($III_1$) according to the diagram:

by the action of a thiol R-SH, optionally in the presence of a reducing agent of the cyclic disulphides, where R can be an alkyl or aryl radical, optionally substituted, (d1) at least one step of condensation of ($III_1'$) with the peptide fragment ($II_2$) in the presence of an aromatic thiol ArSH under conditions in which PG$_1$ is eliminated when it is different from H:

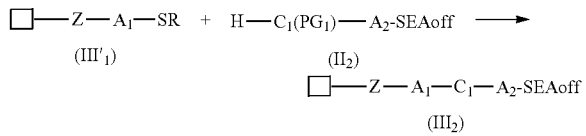

(an−1) at least one step of preparing a fragment $C_{n-1}$(PG$_{n-1}$)-$A_n$ where (PG$_{n-1}$) represents H or a protective group of the thiol of the amino acid $C_{n-1}$, (dn−1) at least one step of condensation of $C_{n-1}$(PG$_{n-1}$)-$A_n$ with $$\square\text{-}Z\text{-}A_1\text{-}C_1\text{-}A_2\text{-} \ldots C_{i-1}\text{-}A_i\text{-} \ldots C_{n-2}A_{n-1}\text{SEAoff} \qquad (III_{n-1})$$

in the presence of an aromatic thiol ArSH under conditions in which PG$_{n-1}$ is eliminated when it is different from H in order to give:

$$\square\text{-}Z\text{-}A_1\text{-}C_1\text{-}A_2\text{-} \ldots C_{i-1}\text{-}A_i\text{-} \ldots C_{n-1}A_n \qquad (IV_n).$$

2. Method according to claim 1, which further comprises:

(e) a step of detaching the peptide $A_1$-$C_1$-$A_2$- . . . $C_{i-1}A_i$- . . . $C_{n-1}A_n$ (I) from the solid support.

3. Method according to claim 1 or claim 2, in which the solid support □ is selected from resins, in particular from resins based on polystyrene, polyacrylamide, polyethylene glycol, cellulose, polyethylene, polyester, latex, polyamide, polydimethylacrylamide, synthetic or natural hydrophilic polymers, glass beads, silica gels.

4. Method according to any one of claims 1 to 3, in which are $C_1, \ldots C_i \ldots C_n$ are cysteines.

5. Method according to any one of claims 1 to 4, in which PG$_1, \ldots$ PG$_i \ldots$ PG$_n$ are tert-butyl sulphenyl groups.

6. Method according to any one of claims 1 to 5, in which:

Y′ comprises a function selected from an azide and Y is selected from the groups comprising an alkyne function, or Y' comprises an alkyne function and Y is selected from the groups comprising an azide function or Y' comprises an aldehyde function, Y is H and the N-terminal amino acid of $A_1$ is selected from a cysteine, a serine or a threonine, or Y' comprises an aldehyde function, Y comprises an $NH_2$ group capable of forming a Schiff base.

7. Method according to any one of claims 1 to 6, in which R is selected from an alkyl radical comprising 1 to 12 carbon atoms, linear or branched, optionally substituted, or C6-C12 aryl, optionally substituted.

8. Method according to any one of claims 1 to 7, in which, for every i=2, . . . n−2, the method comprises (ci) at least one step of conversion of

  (III$_i$)

to

  (III'$_i$)

by the action of a thiol R-SH, optionally in the presence of a reducing agent of cyclic disulphides, (di) at least one step of condensation of $C_i(PG_i)A_{i+1}$SEAoff where ($PG_i$) represents H or a protective group of the thiol of the amino acid $C_i$, with

  (III'$_i$)

in order to give

  (III$_{i+1}$).

9. Method according to any one of claims 1 to 8, in which, for every i=2, . . . n−2, the steps di) of the method are carried out under conditions in which $PG_i$ is removed selectively in situ, without affecting SEAoff and the solvent of the reaction is an aqueous buffer, with pH between 4 and 9, containing an aromatic thiol.

10. Method of manufacturing a medicinal product comprising at least:

manufacturing at least one polypeptide by the method according to any one of claims 1 to 9, and combining it with a pharmaceutically acceptable support.

* * * * *

SEQUENCE LISTING

```
<160> NUMBER OF SEQ ID NOS: 17

<210> SEQ ID NO 1
<211> LENGTH: 10
<212> TYPE: PRT
<213> ORGANISM: Artificial Sequence
<220> FEATURE:
<223> OTHER INFORMATION: Peptide X1

<400> SEQUENCE: 1

Gly Ile Leu Lys Glu Pro Val Gln Gly Ala
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Peptide 9

<400> SEQUENCE: 2

Cys Ile Leu Lys Glu Pro Val His Gly Ala
1               5                   10

<210> SEQ ID NO 3
<211> LENGTH: 36
<212> TYPE: PRT
<213> ORGANISM: Artificial Sequence
<220> FEATURE:
<223> OTHER INFORMATION: Peptide 11a

<400> SEQUENCE: 3

Gly Ile Leu Lys Glu Pro Val Gln Gly Ala Cys His His Leu Glu Pro
1               5                   10                  15

Gly Gly Cys His His Leu Glu Pro Ala Gly Cys Ile Leu Lys Glu Pro
            20                  25                  30

Val His Gly Ala
        35

<210> SEQ ID NO 4
<211> LENGTH: 18
<212> TYPE: PRT
<213> ORGANISM: Artificial Sequence
<220> FEATURE:
```

```
<223> OTHER INFORMATION: Peptide 16a

<400> SEQUENCE: 4

Cys His His Leu Glu Pro Gly Gly Cys Ile Leu Lys Glu Pro Val His
1               5                   10                  15

Gly Ala

<210> SEQ ID NO 5
<211> LENGTH: 94
<212> TYPE: PRT
<213> ORGANISM: Artificial Sequence
<220> FEATURE:
<223> OTHER INFORMATION: Peptide 29
<220> FEATURE:
<221> NAME/KEY: VARIANT
<222> LOCATION: (94)..(94)
<223> OTHER INFORMATION: Xaa is Lys biotinylated

<400> SEQUENCE: 5

Ala Ala Ala Ala Ala Lys Asp Tyr Ile Arg Asn Cys Ile Ile Gly Lys
1               5                   10                  15

Gly Arg Ser Tyr Lys Gly Thr Val Ser Ile Thr Lys Ser Gly Ile Lys
                20                  25                  30

Cys Gln Pro Trp Ser Ser Met Ile Pro His Glu His Ser Phe Leu Pro
            35                  40                  45

Ser Ser Tyr Arg Gly Lys Asp Leu Gln Glu Asn Tyr Cys Arg Asn Pro
        50                  55                  60

Arg Gly Glu Glu Gly Gly Pro Trp Cys Phe Thr Ser Asn Pro Glu Val
65                  70                  75                  80

Arg Tyr Glu Val Cys Asp Ile Pro Gln Cys Ser Glu Val Xaa
                85                  90

<210> SEQ ID NO 6
<211> LENGTH: 11
<212> TYPE: PRT
<213> ORGANISM: Artificial Sequence
<220> FEATURE:
<223> OTHER INFORMATION: Peptide 21
<220> FEATURE:
<221> NAME/KEY: VARIANT
<222> LOCATION: (11)..(11)
<223> OTHER INFORMATION: Xaa is Asn-SEAoff in which SEAoff means
      bis(2-sulfanylethyl)amino cyclic

<400> SEQUENCE: 6

Ala Ala Ala Ala Ala Lys Asp Tyr Ile Arg Xaa
1               5                   10

<210> SEQ ID NO 7
<211> LENGTH: 21
<212> TYPE: PRT
<213> ORGANISM: Artificial Sequence
<220> FEATURE:
<223> OTHER INFORMATION: Peptide 22
<220> FEATURE:
<221> NAME/KEY: VARIANT
<222> LOCATION: (1)..(1)
<223> OTHER INFORMATION: Xaa at position 1 is Cys(StBu) in which StBu
      means terbutylsulfenyl
<220> FEATURE:
<221> NAME/KEY: VARIANT
<222> LOCATION: (21)..(21)
<223> OTHER INFORMATION: Xaa at position 21 is Lys-SEAoff, in which
      SEAoff means bis(2-sulfanylethyl)amino cyclic

<400> SEQUENCE: 7
```

```
Xaa Ile Ile Gly Lys Gly Arg Ser Tyr Lys Gly Thr Val Ser Ile Thr
1               5                   10                  15

Lys Ser Gly Ile Xaa
                20
```

<210> SEQ ID NO 8
<211> LENGTH: 28
<212> TYPE: PRT
<213> ORGANISM: Artificial Sequence
<220> FEATURE:
<223> OTHER INFORMATION: Peptide 25
<220> FEATURE:
<221> NAME/KEY: VARIANT
<222> LOCATION: (1)..(1)
<223> OTHER INFORMATION: Xaa at position 1 is Cys(StBu) in which StBu
      means terbutylsulfenyl
<220> FEATURE:
<221> NAME/KEY: VARIANT
<222> LOCATION: (28)..(28)
<223> OTHER INFORMATION: Xaa at position 28 is Tyr-SEAoff in which
      SEAoff means bis(2-sulfanylethyl)amino cyclic

<400> SEQUENCE: 8

```
Xaa Gln Pro Trp Ser Ser Met Ile Pro His Glu His Ser Phe Leu Pro
1               5                   10                  15

Ser Ser Tyr Arg Gly Lys Asp Leu Gln Glu Asn Xaa
                20                  25
```

<210> SEQ ID NO 9
<211> LENGTH: 34
<212> TYPE: PRT
<213> ORGANISM: Artificial Sequence
<220> FEATURE:
<223> OTHER INFORMATION: Peptide 27
<220> FEATURE:
<221> NAME/KEY: VARIANT
<222> LOCATION: (34)..(34)
<223> OTHER INFORMATION: Xaa is Lys biotinylated

<400> SEQUENCE: 9

```
Cys Arg Asn Pro Arg Gly Glu Glu Gly Gly Pro Trp Cys Phe Thr Ser
1               5                   10                  15

Asn Pro Glu Val Arg Tyr Glu Val Cys Asp Ile Pro Gln Cys Ser Glu
                20                  25                  30

Val Xaa
```

<210> SEQ ID NO 10
<211> LENGTH: 10
<212> TYPE: PRT
<213> ORGANISM: Artificial Sequence
<220> FEATURE:
<223> OTHER INFORMATION: Peptide 4
<220> FEATURE:
<221> NAME/KEY: VARIANT
<222> LOCATION: (10)..(10)
<223> OTHER INFORMATION: Xaa is Ala-SEAoff in which SEAoff is
      bis(2-sulfanylethyl)amino

<400> SEQUENCE: 10

```
Gly Ile Leu Lys Glu Pro Val Gln Gly Xaa
1               5                   10
```

<210> SEQ ID NO 11
<211> LENGTH: 10
<212> TYPE: PRT
<213> ORGANISM: Artificial Sequence
<220> FEATURE:
<223> OTHER INFORMATION: Peptide 2

```
<220> FEATURE:
<221> NAME/KEY: VARIANT
<222> LOCATION: (4)..(4)
<223> OTHER INFORMATION: Xaa is Lys(Boc) in which Boc is
      tert-butoxycarbonyl protection group
<220> FEATURE:
<221> NAME/KEY: VARIANT
<222> LOCATION: (5)..(5)
<223> OTHER INFORMATION: Xaa is Glu(tBu) in which tBu is tert-butyl
      ester protection group
<220> FEATURE:
<221> NAME/KEY: VARIANT
<222> LOCATION: (8)..(8)
<223> OTHER INFORMATION: Xaa is Gln(Trt) in which Trt is trityl
      protection group
<220> FEATURE:
<221> NAME/KEY: VARIANT
<222> LOCATION: (10)..(10)
<223> OTHER INFORMATION: Xaa is Ala-SEAoff in which SEAoff is
      bis(2-sulfanylethyl)amino

<400> SEQUENCE: 11

Gly Ile Leu Xaa Xaa Pro Val Xaa Gly Xaa
1               5                   10

<210> SEQ ID NO 12
<211> LENGTH: 8
<212> TYPE: PRT
<213> ORGANISM: Artificial Sequence
<220> FEATURE:
<223> OTHER INFORMATION: Peptide 7.1
<220> FEATURE:
<221> NAME/KEY: VARIANT
<222> LOCATION: (1)..(1)
<223> OTHER INFORMATION: Xaa is Cys-StBu in which StBu is
      terbutylsulfenyl
<220> FEATURE:
<221> NAME/KEY: VARIANT
<222> LOCATION: (8)..(8)
<223> OTHER INFORMATION: Xaa is Gly-SEAoff in which SEAoff is
      bis(2-sulfanylethyl)amino

<400> SEQUENCE: 12

Xaa His His Leu Glu Pro Gly Xaa
1               5

<210> SEQ ID NO 13
<211> LENGTH: 11
<212> TYPE: PRT
<213> ORGANISM: Artificial Sequence
<220> FEATURE:
<223> OTHER INFORMATION: peptide 17
<220> FEATURE:
<221> NAME/KEY: VARIANT
<222> LOCATION: (6)..(6)
<223> OTHER INFORMATION: Xaa is Lys(Boc) in which Boc is
      tert-butoxycarbonyl protection group
<220> FEATURE:
<221> NAME/KEY: VARIANT
<222> LOCATION: (7)..(7)
<223> OTHER INFORMATION: Xaa is Asp(OtBu) in which OtBu is tert-butyl
      ester protection group
<220> FEATURE:
<221> NAME/KEY: VARIANT
<222> LOCATION: (8)..(8)
<223> OTHER INFORMATION: Xaa is Tyr(tBu) in which tBu is tert-butyl
      ester protection group
<220> FEATURE:
<221> NAME/KEY: VARIANT
<222> LOCATION: (10)..(10)
<223> OTHER INFORMATION: Xaa is Arg(Pbf) in which pBf is protection
      group
<220> FEATURE:
<221> NAME/KEY: VARIANT
<222> LOCATION: (11)..(11)
```

```
<223> OTHER INFORMATION: Xaa is Asn(Trt)-SEAoff in whichTrt is trityl
      protection group and SEAoff is bis(2-sulfanylethyl)amino cyclic

<400> SEQUENCE: 13

Ala Ala Ala Ala Ala Xaa Xaa Xaa Ile Xaa Xaa
1               5                   10

<210> SEQ ID NO 14
<211> LENGTH: 32
<212> TYPE: PRT
<213> ORGANISM: Artificial Sequence
<220> FEATURE:
<223> OTHER INFORMATION: Peptide 23.1
<220> FEATURE:
<221> NAME/KEY: VARIANT
<222> LOCATION: (32)..(32)
<223> OTHER INFORMATION: Xaa is Lys-SEAoff in which SEAoff is
      bis(2-sulfanylethyl)amino cyclic

<400> SEQUENCE: 14

Ala Ala Ala Ala Ala Lys Asp Tyr Ile Arg Asn Cys Ile Ile Gly Lys
1               5                   10                  15

Gly Arg Ser Tyr Lys Gly Thr Val Ser Ile Thr Lys Ser Gly Ile Xaa
            20                  25                  30

<210> SEQ ID NO 15
<211> LENGTH: 60
<212> TYPE: PRT
<213> ORGANISM: Artificial Sequence
<220> FEATURE:
<223> OTHER INFORMATION: Peptide 26.1
<220> FEATURE:
<221> NAME/KEY: VARIANT
<222> LOCATION: (60)..(60)
<223> OTHER INFORMATION: Xaa is Tyr-SEAoff in which SEAoff is
      bis(2-sulfanylethyl)amino cyclic

<400> SEQUENCE: 15

Ala Ala Ala Ala Ala Lys Asp Tyr Ile Arg Asn Cys Ile Ile Gly Lys
1               5                   10                  15

Gly Arg Ser Tyr Lys Gly Thr Val Ser Ile Thr Lys Ser Gly Ile Lys
            20                  25                  30

Cys Gln Pro Trp Ser Ser Met Ile Pro His Glu His Ser Phe Leu Pro
                35                  40                  45

Ser Ser Tyr Arg Gly Lys Asp Leu Gln Glu Asn Xaa
            50                  55                  60

<210> SEQ ID NO 16
<211> LENGTH: 18
<212> TYPE: PRT
<213> ORGANISM: Artificial Sequence
<220> FEATURE:
<223> OTHER INFORMATION: Peptide 8.2
<220> FEATURE:
<221> NAME/KEY: VARIANT
<222> LOCATION: (18)..(18)
<223> OTHER INFORMATION: Xaa is Gly-SEAoff in which SEAoff is
      bis(2-sulfanylethyl)amino

<400> SEQUENCE: 16

Gly Ile Leu Lys Glu Pro Val Gln Gly Ala Cys His His Leu Glu Pro
1               5                   10                  15

Gly Xaa

<210> SEQ ID NO 17
<211> LENGTH: 26
```

```
<212> TYPE: PRT
<213> ORGANISM: Artificial Sequence
<220> FEATURE:
<223> OTHER INFORMATION: Peptide 8.3
<220> FEATURE:
<221> NAME/KEY: VARIANT
<222> LOCATION: (26)..(26)
<223> OTHER INFORMATION: Xaa is Gly-SEAoff in which SEAoff is
      bis(2-sulfanylethyl)amino

<400> SEQUENCE: 17

Gly Ile Leu Lys Glu Pro Val Gln Gly Ala Cys His His Leu Glu Pro
1               5                   10                  15

Gly Gly Cys His His Leu Glu Pro Gly Xaa
            20                  25
```